United States Patent
Feder et al.

(10) Patent No.: US 12,415,811 B2
(45) Date of Patent: Sep. 16, 2025

(54) 1,2,3',5'-TETRAHYDRO-2'H-SPIRO [INDOLE-3,1'-PYRROLO[3,4-C]PYRROLE]-2,3'-DIONE COMPOUNDS AS THERAPEUTIC AGENTS ACTIVATING TP53

(71) Applicant: ADAMED PHARMA, S.A., Czosnow (PL)

(72) Inventors: Marcin Feder, Warsaw (PL); Maria Mazur, Warsaw (PL); Iwona Kalinowska, Warsaw (PL); Joanna Jaszczewska-Adamczak, Warsaw (PL); Wojciech Lewandowski, Grojec (PL); Jakub Witkowski, Warsaw (PL); Sabina Jelen, Warsaw (PL); Katarzyna Wos-Latosi, Lomianki (PL)

(73) Assignee: ADAMED PHARMA S.A., Czosnow (PL)

( * ) Notice: Subject to any disclaimer, the term of this patent is extended or adjusted under 35 U.S.C. 154(b) by 1110 days.

(21) Appl. No.: 16/962,647

(22) PCT Filed: Jan. 9, 2019

(86) PCT No.: PCT/EP2019/050370
§ 371 (c)(1),
(2) Date: Jul. 16, 2020

(87) PCT Pub. No.: WO2019/141549
PCT Pub. Date: Jul. 25, 2019

(65) Prior Publication Data
US 2020/0354372 A1  Nov. 12, 2020

(30) Foreign Application Priority Data

Jan. 16, 2018 (EP) .................................... 18461506

(51) Int. Cl.
*A61P 35/00* (2006.01)
*C07D 487/20* (2006.01)

(52) U.S. Cl.
CPC ............ *C07D 487/20* (2013.01); *A61P 35/00* (2018.01)

(58) Field of Classification Search
CPC ..... C07D 487/20; C07D 487/10; A61P 35/00; A61P 37/00; A61K 31/4439; A61K 31/50; A61K 31/506
See application file for complete search history.

(56) References Cited

FOREIGN PATENT DOCUMENTS

| | | | |
|---|---|---|---|
| JP | 2017517555 A | 6/2017 | |
| WO | WO 2011/134925 A1 | 11/2011 | |
| WO | WO 2012/155066 A2 | 11/2012 | |
| WO | WO 2015/189799 | * 12/2015 | ........... C07D 487/10 |
| WO | WO-2015189799 A1 | * 12/2015 | ............. A61P 17/00 |

OTHER PUBLICATIONS

International Search Report issued by the International Searching Authority (ISA/O.E.P.M. ) on Feb. 18, 2019 in connection with International Application No. PCT/ES2019/050370.
PCT International Publication No. WO 2015/189799 A1, Adamed SP Z.O.O. [PL/PL], published Dec. 17, 2015 (Exhibit 1).
PCT International Publication No. WO 2012/155066 A2, Wang Shaomeng [US/US], published Nov. 15, 2012 (Exhibit 2).
PCT International Publication No. WO 2011/134925 A1, F. Hoffmann-LA Roche AG [CH/CH], published Nov. 3, 2011 (Exhibit 3) ; and.
International Search Report issued by the International Searching Authority (ISA/O.E.P.M.) on Feb. 18, 2019 in connection with International Application No. PCT/ES2019/050370 (Exhibit 4).
Feb. 26, 2024 Notice of Non-Final Rejection issued by the Korean Intellectual Property Office in connection with Korean Patent Application No. 10-2020-7020046 (including English language translation).
Apr. 9, 2024 Patent Examination Report 1 issued by the New Zealand Intellectual Property Office in connection with New Zealand Patent Application No. 765577.

* cited by examiner

Primary Examiner — Alma Pipic
(74) Attorney, Agent, or Firm — Gary J. Gershik

(57) ABSTRACT

The invention relates to 1,2,3',5'-tetrahydro-2'H-spiro[indole-3,1'-pyrrolo[3,4-c]pyrrole]-2,3'-dione compounds represented by formula (I), wherein all symbols and variables are as defined in the description. The compounds can find use in a method of prevention and/or treatment of diseases selected from the group consisting of cancer, immune diseases, inflammatory conditions, allergic skin diseases associated with excessive proliferation, blinding disease and viral infections.

Formula (I)

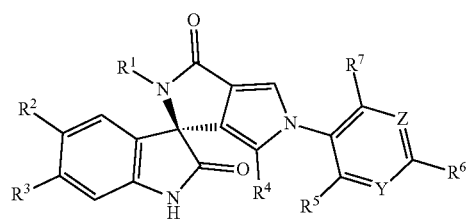

20 Claims, 2 Drawing Sheets

1,2,3',5'-TETRAHYDRO-2'H-SPIRO[INDOLE-3,1'-PYRROLO[3,4-C]PYRROLE]-2,3'-DIONE COMPOUNDS AS THERAPEUTIC AGENTS ACTIVATING TP53

RELATED APPLICATIONS

This application is a § 371 national stage of PCT International Application No. PCT/EP2019/050370, filed Jan. 9, 2019, claiming priority of European Patent Application Ser. No. 18/461,506.0, filed Jan. 16, 2018, the contents of each of which are hereby incorporated by reference into this application.

FIELD OF THE INVENTION

The present invention relates to new 1,2,3'5'-tetrahydro-2'H-spiro[indole-3,1'-pyrrolo[3,4-c]pyrrole]-2,3'-dione compounds and these compounds for use as medicament, especially for the treatment of diseases in which the p53-Mdm2 protein-protein interactions are disturbed and/or which are sensitive to inhibition of the p53-Mdm2 interactions, including proliferative diseases such as cancer. Furthermore, the present invention provides pharmaceutical compositions comprising the aforementioned compounds.

BACKGROUND OF THE INVENTION p53 is a transcription factor that responds to cellular stress by regulating the transcription of numerous genes that determine cells fate. In stress conditions p53 can trigger cell cycle arrest and DNA repair processes or cell death programs like apoptosis or senescence. The choice between these responses depends on the type and intensity of stress signals. In human cells p53 activity is strictly controlled by its negative regulator the protein named Mdm2. Mdm2 forms a tight complex with the p53 trans-activation domain, blocking its ability to regulate target genes and to exert antiproliferative effects. Additionally, Mdm2 promotes the nuclear export and rapid degradation of p53 by the ubiquitin-proteasome system.

Being a key player in the cellular response to stress, p53 serves as the major obstruction for tumorigenesis. Patients with Li-Fraumeni syndrome which inherit mutated p53 are very susceptible to cancer. Mice with damaged p53 gene appear normal but are prone to the spontaneous development of a variety of neoplasms by 6 months of age. This prominent tumor suppressive role of p53 causes that its function is disabled in virtually all human cancers, either through mutation of the p53 gene or through aberrant expression of proteins acting as its negative regulators such as Mdm2.

Amplification of the Mdm2 gene is reported in more than 10% of 8000 various human cancers, including sarcomas, lung and stomach tumors, wherein p53 gene is not damaged. Multiple other tumors acquire a single nucleotide polymorphism in the Mdm2 promoter that leads to 2-3 fold increase in Mdm2 expression correlates with accelerated tumor formation. These alterations are perceived as the major mechanisms for inhibition of the p53 function in cancers retaining wild-type p53.

Functional genetic studies on mice have shown that restoration of inactivated p53 is sufficient to cause rapid regression of several different tumor types. Following this line, targeting the p53-Mdm2 interaction by small molecules to release and reactivate p53 has emerged as promising therapeutic strategy to treat human cancers that are p53 wild-type. Several groups of small-molecule non-peptide inhibitors of p53-Mdm2 interaction have been reported in recent years including nutlins, piperazine-4-phenyl derivatives, chalcones, sulphonamides, benzodiazepinediones, spiro-oxindoles. MDM2 inhibitors yield both common and different cellular responses in normal and tumor cells that are in agreement with the previous results from genetics studies. In normal cells, the activation of p53 by MDM2 inhibitors induces cell cycle arrest but not cell death. In tumor cells, the activation of p53 by the inhibitors induces not only cell cycle arrest but also cell death. This profile provides an outlook for high selectivity and low toxicity of the potential therapy. Nevertheless, none of these Mdm2 antagonists proved its effectiveness in human clinical trials. Thus, there is still a need for new compounds with increased potency, favorable pharmacokinetics and toxicity profile.

Our previous application WO2015/189799 discloses compounds comprising 1,1',2,5-tetrahydrospiro[indole-3,2'-pyrrole]-2,5'-dione system that show potent and specific antitumor activity in in vitro studies. However, further studies revealed that their in vivo efficacy is moderate and the most effective compounds exhibit unacceptable high clearance in human microsomes that preclude their clinical efficacy.

Therefore, there is still a need for compounds with excellent in vitro activity having improved pharmacokinetics and thus exhibiting outstanding anticancer efficacy both in mice in vivo models and future clinical trials.

The present invention solves the problem by providing new compounds having 1,2,3',5'-tetrahydro-2'H-spiro[indole-3,1'-pyrrolo[3,4-c]pyrrole]-2,3'-dione system.

SUMMARY OF THE INVENTION

In the first aspect, the present invention provide a compound having the following structure

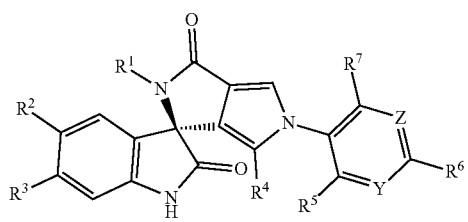

Formula (I)

wherein
R$^1$ is meta-halo-phenyl that is optionally further substituted by one to two substituents independently selected from the group consisting of halogen, —OH, —NH$_2$, —NO$_2$, —CN, —C$_1$-C$_6$-alkyl, —O—(C$_1$-C$_6$-alkyl), —S—(C$_1$-C$_6$-alkyl), —C(O)O—(C$_1$-C$_6$-alkyl), —NH(C$_1$-C$_6$-alkyl), and —N(C$_1$-C$_6$-alkyl)$_2$,
R$^2$ and R$^3$ are independently H or halogen;
R$^4$ is —C$_1$-C$_6$-alkyl;
R$^7$ is —OCH$_3$;
R$^5$, R$^6$, R$^8$, R$^9$ are independently H, halogen, —OCH$_3$, —NH(CH$_3$), or —N(CH$_3$)$_2$.
Z is C—R$^8$ or N, Y is C—R$^9$ or N, with the proviso that Z is not C—R$^8$ and Y is not C—R$^9$ at the same time,
Preferably, in formula (I), R$^1$ is meta-halo-phenyl that is optionally further substituted by one to two substituents independently selected from the group consisting of halogen, —C$_1$-C$_6$-alkyl, —O—(C$_1$-C$_6$-alkyl), —NH(C$_1$-C$_6$-alkyl), and —N(C$_1$-C$_6$-alkyl)$_2$. More preferably, in definition of R$^1$ substituent in formula (I), C$_1$-C$_6$-alkyl C$_1$-C$_3$-alkyl.

Even more preferably, in formula (I), $R^1$ is meta-halophenyl that is optionally further substituted by one to two substituents independently selected from the group consisting of halogen, —$CH_3$, —$OCH_3$, —$NH(CH_3)$, and —$N(CH_3)_2$. Even more preferably, $R^1$ is meta-halo-phenyl that is optionally further substituted by one to two substituents independently selected from the group consisting of halogen, —$CH_3$, and —$OCH_3$. Most preferably, $R^1$ is meta-halo-phenyl that is optionally further substituted by one to two substituents independently selected from the group consisting of halogen.

Preferably, in formula (I), $R^2$ is H, and $R^3$ is Cl.

Preferably, in formula (I), $R^4$ is iso-propyl or iso-butyl.

Preferably, in formula (I), Z and Y are both N. More preferably, in such embodiment, $R^5$ and $R^6$ are both —$OCH_3$.

Preferably, in formula (I), Z is C—$R^8$ and Y is N. More preferably, in such embodiment, $R^8$ is H, and at least one of $R^5$ and $R^6$ is —$OCH_3$, and the second is selected from H, —$N(CH_3)_2$, and —$OCH_3$.

As a specific compound of the invention, one of the following group can be mentioned:

(1) (3S)-6-chloro-2'-(3-chlorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione (2) (3S)-6-chloro-2'-(5-chloro-2-fluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione (3) (3S)-6-chloro-2'-(5-chloro-2-methylphenyl)-6'-(propan-2-yl)-5'-(2,4,6-trimethoxypyrimidin-5-yl)-1,2,3',5'-tetrahydro-2'H-spiro[indole-3,1'-pyrrolo[3,4-c]pyrrole]-2,3'-dione (4) (3S)-6-chloro-2'-(3-chloro-4-fluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione (5) (3S)-6-chloro-2'-(5-chloro-2-fluorophenyl)-6'-(propan-2-yl)-5'-(2,4,6-trimethoxypyrimidin-5-yl)-1,2,3',5'-tetrahydro-2'H-spiro[indole-3,1'-pyrrolo[3,4-c]pyrrole]-2,3'-dione (5) (3S)-6-chloro-2'-(5-chloro-2-fluorophenyl)-5'-[6-(dimethylamino)-4-methoxypyridin-3-yl]-6'-(propan-2-yl)-1,2,3',5'-tetrahydro-2'H-spiro[indole-3,1'-pyrrolo[3,4-c]pyrrole]-2,3'-dione (6) (3S)-6-chloro-2'-(3,4-difluorophenyl)-5'-(2,4-dimethoxypyrimidin-5-yl)-6'-(propan-2-yl)-1,2,3,5'-tetrahydro-2'H-spiro[indole-3,1'-pyrrolo[3,4-c]pyrrole]-2,3-dione (7) (3S)-6-chloro-2'-(3,4-difluorophenyl)-5'-(4,6-dimethoxypyridin-3-yl)-6'-(propan-2-yl)-1,2,3',5'-tetrahydr-2'H-spiro[indole-3,1'-pyrrolo[3,4-c]pyrrole]-2,3'-dione (8) (3S)-6-chloro-2'-(5-chloro-2-fluorophenyl)-5'-(4,6-dimethoxypyridin-3-yl)-6'-(propan-2-yl)-1,2,3',5'-tetrahydro-2'H-spiro[indole-3,1'-pyrrolo[3,4-c]pyrrole]-2,3'-dione (9) (3S)-6-chloro-2'-(5-chloro-2,4-difluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

(10) (3S)-6'-(butan-2-yl)-6-chloro-2'-(5-chloro-2-fluorophenyl)-5'-(2,4-dimethoxypyrimidin-5-yl)-1,2,3',5'-tetrahydro-2'H-spiro[indole-3,1'-pyrrolo[3,4-c]pyrrole]-2,3'-dione As a more specific compound of the invention, one of the following group can be mentioned:

(1) (3S)-6-chloro-2'-(3-chlorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione (2) (3S)-6-chloro-2'-(5-chloro-2-fluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione (3) (3S)-6-chloro-2'-(5-chloro-2-methylphenyl)-6'-(propan-2-yl)-5'-(2,4,6-trimethoxypyrimidin-5-yl)-1,2,3',5'-tetrahydro-2'H-spiro[indole-3,1'-pyrrolo[3,4-c]pyrrole]-2,3'-dione (4) (3S)-6-chloro-2'-(3-chloro-4-fluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione (5) (3S)-6-chloro-2'-(5-chloro-2-fluorophenyl)-6'-(propan-2-yl)-5'-(2,4,6-trimethoxypyrimidin-5-yl)-1,2,3',5'-tetrahydro-2'H-spiro[indole-3,1'-pyrrolo[3,4-c]pyrrole]-2,3'-dione (7) (3S)-6-chloro-2'-(3,4-difluorophenyl)-5'-(2,4-dimethoxypyrimidin-5-yl)-6'-(propan-2-yl)-1,2,3,5'-tetrahydro-2'H-spiro[indole-3,1'-pyrrolo[3,4-c]pyrrole]-2,3'-dione

(10) (3S)-6-chloro-2'-(5-chloro-2,4-difluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

(11) (3S)-6'-(butan-2-yl)-6-chloro-2'-(5-chloro-2-fluorophenyl)-5'-(2,4-dimethoxypyrimidin-5-yl)-1,2,3',5'-tetrahydro-2'H-spiro[indole-3,1'-pyrrolo[3,4-c]pyrrole]-2,3'-dione Alternatively, as a more specific compound of the invention, one of the following group can be mentioned:

(6) (3S)-6-chloro-2'-(5-chloro-2-fluorophenyl)-5'-[6-(dimethylamino)-4-methoxypyridin-3-yl]-6'-(propan-2-yl)-1,2,3',5'-tetrahydro-2'H-spiro[indole-3,1'-pyrrolo[3,4-c]pyrrole]-2,3'-dione (8) (3S)-6-chloro-2'-(3,4-difluorophenyl)-5'-(4,6-dimethoxypyridin-3-yl)-6'-(propan-2-yl)-1,2,3',5'-tetrahydro-2'H-spiro[indole-3,1'-pyrrolo[3,4-c]pyrrole]-2,3'-dione (9) (3S)-6-chloro-2'-(5-chloro-2-fluorophenyl)-5'-(4,6-dimethoxypyridin-3-yl)-6'-(propan-2-yl)-1,2,3',5'-tetrahydro-2'H-spiro[indole-3,1'-pyrrolo[3,4-c]pyrrole]-2,3'-dione The particularly preferable compound of the invention is a compound represented by the following structure

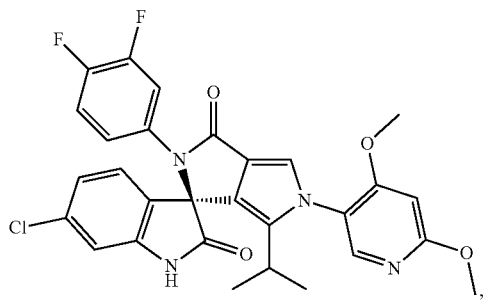 [SMILES: COc1cc(OC)c(-n2cc3c(c2C(C)C)[C@@]2(C(=O)Nc4cc(Cl)ccc42)N(c2ccc(F)c(F)c2)C3=O)cn1]

which means (3S)-6-chloro-2'-(3,4-difluorophenyl)-5'-(4,6-dimethoxypyridin-3-yl)-6'-(propan-2-yl)-1,2,3',5'-tetrahydro-2'H-spiro[indole-3,1'-pyrrolo[3,4-c]pyrrole]-2,3'-dione.

The second particularly preferable compound of the invention is a compound represented by the following structure

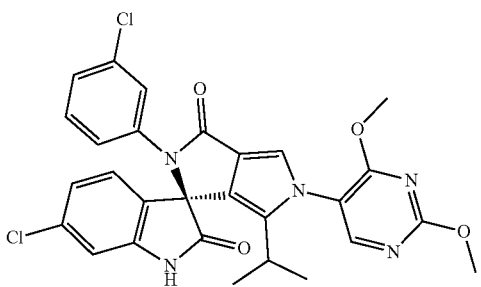 [SMILES: COc1ncc(-n2cc3c(c2C(C)C)[C@@]2(C(=O)Nc4cc(Cl)ccc42)N(c2cccc(Cl)c2)C3=O)c(OC)n1]

which means (3S)-6-chloro-2'-(3-chlorophenyl)-5'-(2,4-dimethoxypyrimidin-5-yl)-6'-(propan-2-yl)-1,2,3',5'-tetrahydro-2'H-spiro[indole-3,1'-pyrrolo[3,4-]pyrrole]-2,3'-dione.

Another aspect of the invention relates to a compound of formula (I) for use as a medicament.

Preferably, the medicament is useful for the prevention and/or treatment of diseases selected from the group consisting of cancer, immune diseases, inflammatory conditions, allergic skin diseases associated with excessive proliferation, blinding disease, and viral infections.

The next aspect of the invention relates to a pharmaceutical composition comprising as an active ingredient a compound of formula (I) in combination with at least one pharmaceutically acceptable excipient.

The last aspect of the invention relates to a method of treatment and/or prevention of diseases selected from the group consisting of cancer, immune diseases, inflammatory conditions, allergic skin diseases associated with excessive proliferation, blinding disease, and viral infections, comprising administration of a therapeutically effective amount of a compound of formula (I) or a pharmaceutical composition as defined above.

SHORT DESCRIPTION OF FIGURES

DETAILED DESCRIPTION OF THE INVENTION

Figure 1:
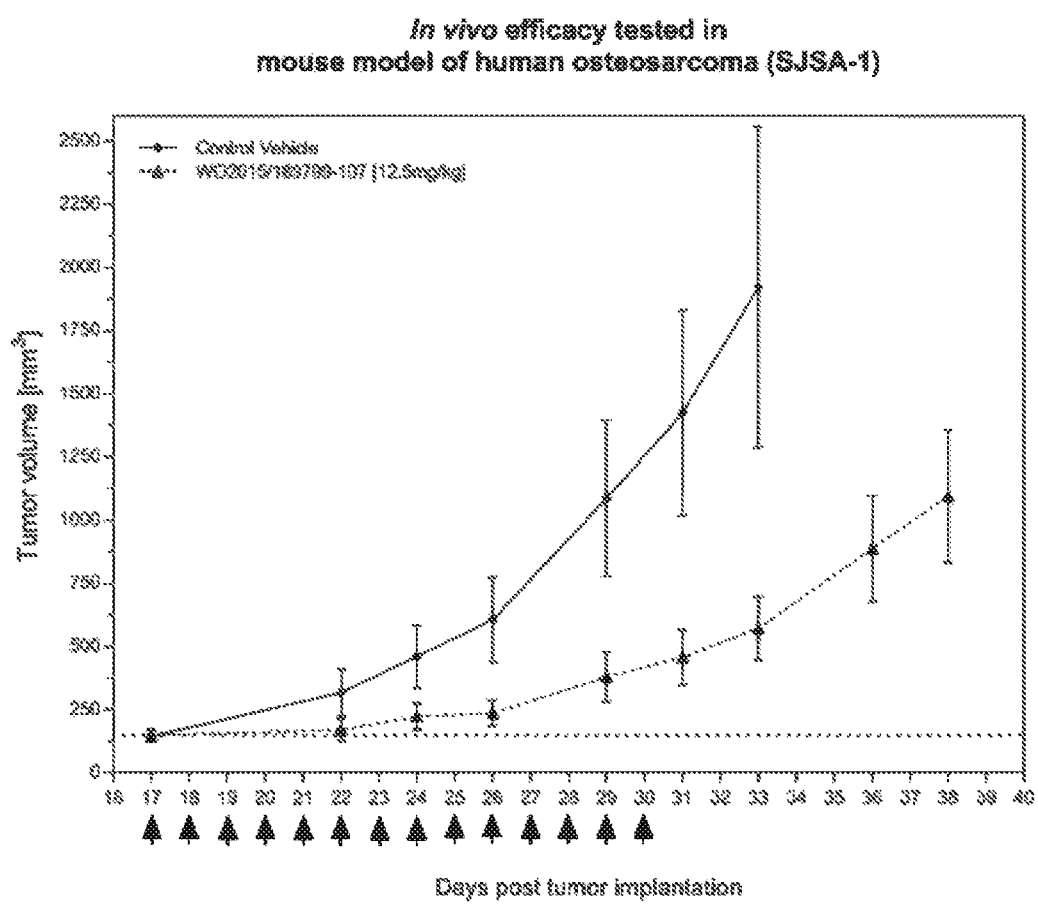
FIG. 1 shows in vivo efficacy for Compound 107 from International Publication WO2015/189799 as a Reference Compound in mouse model of human osteosarcoma (SJSA-1). SJSA-1 cells were inoculated subcutaneously (s.c.) in amount of $3 \times 10^6$/mouse; tested compound was administered orally (p.o.) in a q1d×14 schedule; 7 mice per group.

Where the compounds of the invention can exist in one or more tautomeric forms, all such forms although not explicitly indicated in the above formula are within the scope of the present invention. Accordingly, the compounds may be present as a mixture of tautomers or as a individual tautomer.

The terms used in the present invention have the following meanings. Other terms not defined below have the meanings as those understood by those skilled in the art.

The term "$C_1$-$C_6$-alkyl" is a saturated, straight or branched chain hydrocarbon having 1 to 6 carbon atoms. Examples of $C_1$-$C_6$-alkyl are methyl, ethyl, n-propyl, iso-propyl, n-butyl, tert-butyl, sec-butyl, n-pentyl and n-hexyl. More preferably, $C_1$-$C_6$-alkyl is a $C_1$-$C_4$-alkyl, $C_1$-$C_3$-alkyl, or $C_1$-$C_2$-alkyl. Notation $C_1$-$C_4$-alkyl, $C_1$-$C_3$-alkyl, $C_1$-$C_2$-alkyl means a saturated, straight or branched chain hydrocarbon having 1 to 4, 3 or 2 carbon atoms, respectively. Most preferably, the $C_1$-$C_6$-alkyl is $C_1$-alkyl that is methyl group (abbreviated as Me).

The term "halogen" is selected from F, Cl, Br and I Preferably, the halogen is selected from F and Cl.

The term "m-halo-phenyl" as present in definition of group $R^1$ means phenyl group that is substituted by a halogen as defined above in meta position in relation to the point of attachment of the phenyl group to the nitrogen atom of the pyrrolo[3,4-c]pyrrole ring system.

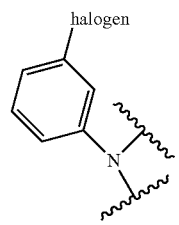

Expression "Z is C—$R^8$ or N, Y is C—$R^9$ or N, with the proviso that Z is not C—$R^8$ and Y is not C—$R^9$ at the same time" means that in the compound of the invention, Z is C—$R^8$ and Y is N, or Z is N and Y is C—$R^9$, or Z is N and Y is N.

Since compounds of the invention may be acidic or basic they can form suitable acid addition salts with a base or an acid, respectively.

Pharmaceutically acceptable acid addition salt refers to those salts which retain the biological effectiveness of the free bases and which are not biologically undesirable. Acid addition salts may be formed with inorganic (mineral) acids or organic acids. As examples of acids, may be mentioned hydrochloric, hydrobromic, hydroiodic, phosphoric, sulfuric, nitric, carbonic, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, pamoic, xinafoic, hexanoic acid.

An acid addition salt may be prepared in a simple manner by reacting a compound of formula (I) with a suitable inorganic or organic acid in an amount substantially equimolar to the compound of formula (I), optionally in a suitable solvent such as an organic solvent to form a salt which is usually isolated for example by crystallisation and filtration. For example, the free bases of the compounds can be converted into the corresponding hydrochloride salts by treating a solution of the compound, for example, in methanol, with a stoichiometric amount of hydrochloric acid or hydrogen chloride in methanol, ethanol or diethyl ether, followed by evaporation of solvents.

Similarly, pharmaceutically acceptable base addition salts include salts derived from inorganic bases such as sodium, potassium, lithium, ammonium, calcium, magnesium, iron, zinc, copper, manganese, aluminium and the like. Salts derived from pharmaceutically acceptable non-toxic organic bases include salts of primary, secondary, and tertiary amines including naturally occurring substituted amines, cyclic amines and basic ion exchange resins, such as isopropylamine, trimethylamine, diethylamine, triethylamine, tripropylamine, and ethanolamine and triethanolamine.

Compounds of formula (I) can be obtained using the following methods.

Compounds based on 1',2,5'-tetrahydrospiro[indolo-3,2'-pyrrolo]-2,5'-dione fused with pyrrole ring (compounds of formula (I)) can be obtained according to the following Reaction Scheme 1.

Initially, methyl ketone C-1 was treated with isatin C-2 in the presence of a base, typically diethylamine (DEA) or lithium bis(trimethylsilyl)amide (LiHMDS).

The resulting aldol C-3 was subsequently dehydrated under acidic conditions using typically conc. hydrochloric acid (12 M), providing to unsaturated compound C-4.

In parallel, an amide C-6 was prepared by coupling of an amine C-5 with prop-2-ynoic acid, preferably by the use of coupling reagents, typically carbodiimide reagents like dicy-

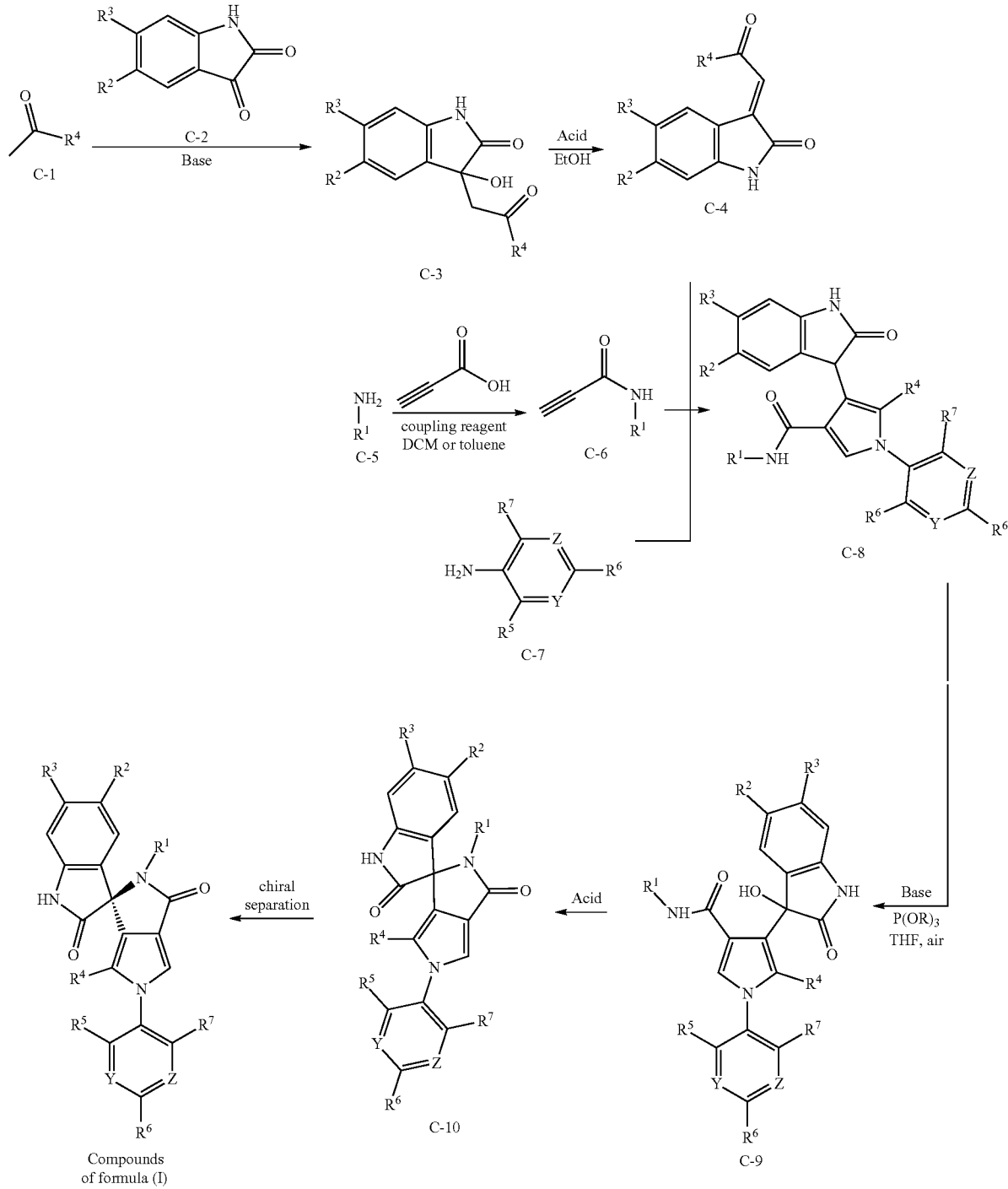

clohexylcarbodiimide (DCC) or (3-dimethylaminopropyl)-N'-ethylcarbodiimide hydrochloride (EDC.HCl).

Hydroamination of the alkyne C-6 with the amine C-7 and subsequent reaction with the enone C-4, leads to a substituted pyrrole C-8. This one-pot reaction can be performed typically in acetic acid under microwave irradiation.

The intermediate C-8 can be oxidized to 3-hydroxy-2-oxindole derivative in the presence of an excess of a base, typically sodium tert-butoxide, appropriate trialkyl phosphite, typically trimethyl or triethyl phosphite, and atmospheric oxygen.

Such prepared compounds C-9 were cyclized in acidic medium, typically trifluoroacetic acid, giving desired racemic fused spirocyclic oxindoles.

Finally, the desirable S-enantiomer was separated using chiral HPLC conditions.

More details as to preparation of 1,1',2,5'-tetrahydrospiro[indolo-3,2'-pirolo]-2,5'-dione core have been described in our previous patent application WO 2015/189799 A1.

Respective ketones C-1, isatines C-2 and amines are commercially available or can be obtained using the following methods.

Scheme 2 illustrates one representative method for the preparation of 5-amino-2,4-dimethoxypyrimidine (C-7A) via nucleophilic substitution of chlorine at 2 and 4 position in the 2,4-dichloro-5-nitropyrimidine (C-7A1) by methoxy group, and subsequent reduction of nitro group in the 2,4-dimethoxy-5-nitropyrimidine (C-7A2).

Reaction Scheme 2.

Reaction Scheme 3.

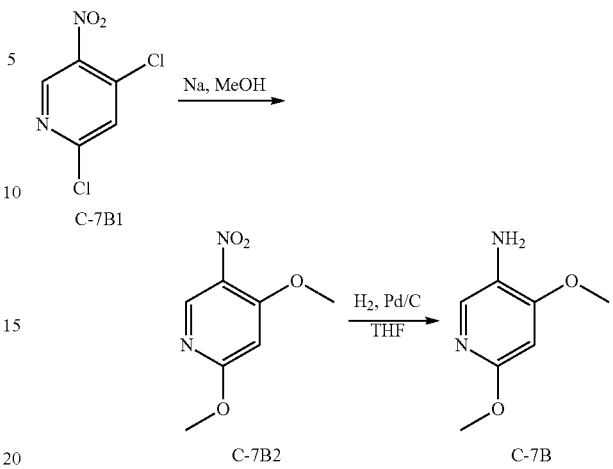

Scheme 4 illustrates a representative method for the preparation of 5-amino-4-methoxy-2-(dimethylamino)pyridine (C-7C) via nucleophilic substitution of chlorine at 2 position in the 2-chloro-4-methoxy-5-nitropyridine (C-7C1) by methoxy group and subsequent reduction of nitro group in the 4-methoxy-2-(dimethylamino)-5-nitropyridine (C-7C2).

Reaction Scheme 4.

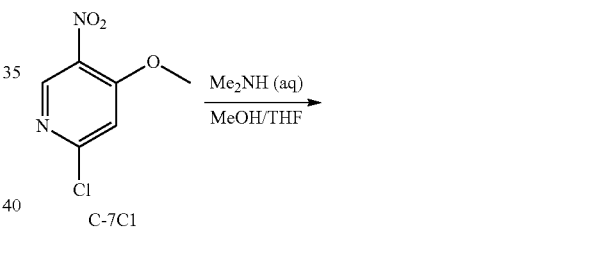

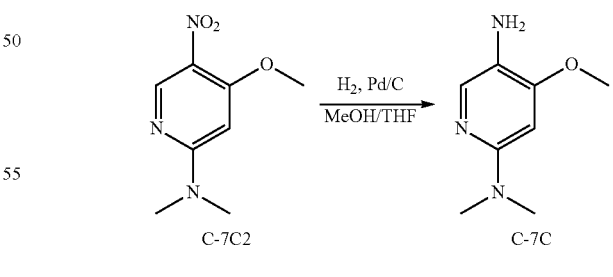

Scheme 3 illustrates a representative method for the preparation of 3-amino-4,6-dimethoxypyridine (C-7B) via nucleophilic substitution of chlorine at 2 and 4 position in the 2,4-dichloro-5-nitropyridine (C-7B1) by methoxy group, followed by reduction of nitro group in the 2,4-dimethoxy-5-nitropyridine (C-7B2).

Scheme 5 illustrates a representative method for the preparation of 5-amino-2,4,6-trimethoxypyrimidine (C-7D) via nitration of 2-chloro-4,6-dimethoxypyrimidine (C-7D1) at 5 position, following the nucleophilic substitution of chlorine at 2 position in the 2-chloro-4,6-dimethoxy-5-nitropyrimidine (C-7D2) by methoxy group. The last step was the reduction of nitro group in the 2,4,6-trimethoxy-5-nitropyrimidine (C-7D3).

Reaction Scheme 5.

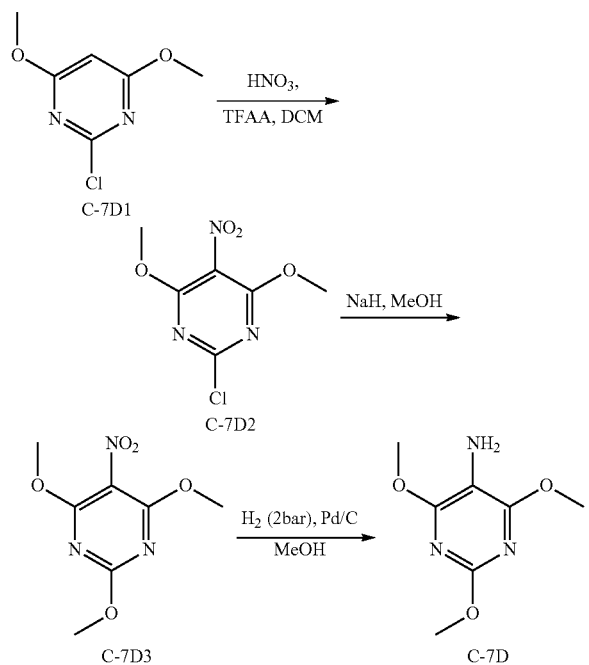

As mentioned above, the compounds of the invention are for use as a medicament that is useful for the prevention and/or treatment of diseases selected from the group consisting of cancer, immune diseases, inflammatory conditions, allergic skin diseases associated with excessive proliferation, blinding disease and viral infections.

In particular, the compounds according to the invention are useful for the prevention and/or treatment of diseases associated with dysregulation of the cell cycle and apoptosis, i.e. immune diseases such as for example autoimmune diseases and conditions associated with the rejection of tissue/organ transplant such as rheumatoid arthritis, graft-versus-host disease, systemic lupus erythematosus, Sjorgen's syndrome, multiple sclerosis, Hashimoto's thyreoiditis, polymyositis; chronic inflammatory conditions are asthma, osteoarthritis, atherosclerosis, Morbus Crohn; inflammatory or allergic conditions of the skin are psoriasis, contact dermatitis, atopic dermatitis, alopecia areata, erythema multiforma, dermatitis herpetiformis, scleroderma, vitiligo, hypersensitivity angiitis, urticarial, bullous pemphigoid, pemphigus, epidermolysis bullosa acquisita; hyperproliferative disorder is Li-Fraumeni syndrome; cancer or tumor diseases are benign or malignant tumors, sarcomas, such as rhabdomyosarcoma, bone cancer, e.g., osteosarcomas, carcinoma of the brain, e.g., soft tissue brain tumor, kidney, liver, adrenal gland, bladder, breast, stomach, gastric tumors, ovaries, colon, rectum, prostate, pancreas, lung, vagina or thyroid, glioblastomas, multiple myeloma, gastrointestinal cancer, especially colon carcinoma or colorectal adenoma, a tumor of the neck and head, melanoma, prostate hyperplasia, a neoplasia, a neoplasia of epithelial character, a mammary carcinoma, a leukemia, such as B- or T-cell lymphomas, polycythemia vera, thrombocythemia, adrenocortical carcinoma, including metastasis in other organs, respectively; proliferative vitreoretinopathy, viral infections are herpes, papilloma, HIV, hepatitis.

In the treatment of the above-mentioned diseases, the compounds of the invention can be administered as a chemical compound, but typically will be used in the form of pharmaceutical compositions, comprising a compound according to the invention or a pharmaceutically acceptable salt thereof as defined above as active ingredient, in combination with pharmaceutically acceptable carriers and excipients.

In the treatment of the abovementioned diseases, the pharmaceutical compositions of the invention they can be administered by any route, preferably orally or parenterally, and will have the form of a preparation intended for use in medicine, depending upon the intended route of administration.

Solid preparations can take the form of, for example, tablets or capsules prepared by conventional means with pharmaceutically acceptable inactive ingredients such as binding agents (e.g., pregelatinized maize starch, polyvinylpyrrolidone or hydroxypropyl methylcellulose); fillers (e.g., lactose, sucrose, carboxymethylcellulose, microcrystalline cellulose or calcium hydrogen phosphate); lubricants (e.g., magnesium stearate, talc or silica); disintegrants (e.g., crospovidone, potato starch or sodium starch glycolate); wetting agents (e.g., sodium lauryl sulphate). The tablets may be coated according to methods well known in the art with conventional coatings, coatings for delaying/controlling release or enteric coatings. Liquid preparations for oral administration may take the form of, for example, solutions, syrups or suspensions, or may be presented as a dry product for reconstitution with water or other suitable vehicle before use. Such liquid preparations may be prepared by conventional means with pharmaceutically acceptable inactive ingredients such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl p- or propyl hydroxybenzoate or sorbic acid). Preparations may also comprise suitable buffers, flavoring agents, coloring agents, and sweeteners.

Preparations for oral administration may be suitably formulated by methods known to those skilled in the art to obtain a controlled release of the active compound.

Parenteral administration includes administration by intramuscular and intravenous injection and infusion (infusion) intravenous. Formulations for parenteral administration may be in unit dosage form, for example, in ampoules or in multidose containers, with a preservative added. The compositions may take forms of suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g., sterile pyrogen-free water.

The method of treatment using the compounds of this invention will involve administration of a therapeutically effective amount of a compound of the invention, preferably in the form of a pharmaceutical composition to a subject in need of such treatment.

A proposed dose of the compounds of the present invention is from about 0.1 to about 1000 mg per day, in single or divided doses. The skilled person will appreciate that the selection of the dose required to achieve the desired biological effect will depend on a number of factors, for example the specific compound, the use, the mode of administration, the age and condition of the patient and the precise dosage will be ultimately determined at the discretion of the attendant physician.

EXAMPLES

The following examples are not intended to limit the invention, but merely serve as illustration of the present invention.

Abbreviations

AcOEt ethyl acetate
AcOH acetic acid
br s broad singlet
$CaCl_2$ calcium chloride
$CHCl_3$ chloroform
d doublet
dd doublet of doublets
ddd doublet of doublet of doublets
dq doublet of quartets
DEA N,N'-diethylamine
DCC N,N'-dicyclohexylcarbodiimide
DCM dichloromethane
EDC.HCl N-(3-Dimethylaminopropyl)-N'-ethylcarbodiimide hydrochloride
EtOH ethanol
eq equivalents
ESI electrospray ionization
h hour(s)
HCl hydrogen chloride
HPLC High-Performance Liquid Chromatography
L litre
LiHMDS lithium bis(trimethylsilyl)amide
m multiplet
MeOH methanol
$MgSO_4$ magnesium sulfate
mL milliliter(s)
MsOH methanesulfonic acid
MW microwave
$NaHCO_3$ sodium bicarbonate
NaOH sodium hydroxide
$Na_2SO_4$ sodium sulfate
NMR Nuclear Magnetic Resonance
NP HPLC Normal-Phase High-Performance Liquid Chromatography
—OMe methoxy group —OEt ethoxy group
p.a. Puriss pro anlysi
$PTSA.H_2O$ p-toluenesulfonic acid monohydrate
q quartet
RP-HPLC Reversed-Phase High-Performance Liquid Chromatography
s singlet
sep septet
SFC Supercritical Fluid Chromatography
SQD MS Single Quadrupole Detector Mass Spectrometer
t triplet
TFA trifluoroacetic acid
TFAA trifluoroacetic anhydride
THF tetrahydrofuran
TLC Thin-Layer Chromatography
UPLCMS Ultra Performance Liquid Chromatography Mass Spectrometry
μL microliter TLC were performed with silica gel 60 $F_{254}$ on aluminum foils (Sigma-Aldrich, Merck) using appropriate solvent systems. Visualization was generally done by UV light (254 nm).

UPLC-Ms Method:

UPLCMS analyses were performed on a UPLC liquid chromatograph equipped with PDA detector and SQD MS detector, operating under ESI(+) or ESI(−) using C18 column, 2.1 mm×100 mm, 1.7 μm (AQUITY UPLC BEH or equivalent). HPLC or LC/MS grade methanol, HPLC grade water, HPLC or LC/MS grade formic acid, p.a. grade 25% solution of ammonia and mixture of them were used as a mobile phase. Operating conditions were the following: mobile phase flow 0.45 mL/min, wavelength 210-400 nm, injection volume 1 μL, column temperature 60° C., autosampler temperature 5° C. The analysis was conducted 5.5 min+1.5 min for "the delay of the next injection". Gradient elution with a linear course:

| Time [min] | % A | % B | Gradient curve |
|---|---|---|---|
| 0.0 | 80.0 | 20.0 | — |
| 4.0 | 0.1 | 99.9 | linear (6) |
| 5.5 | 80.0 | 20.0 | immediate (11) |

The solutions were prepared as follows:

Preparation of the mobile phase A1—basic gradient: 25 μL of formic acid and 250 μL of 25% ammonia solution were added to 250 mL of water. Degas using an ultrasonic bath for 10 min.

Preparation of the mobile phase A2—acidic gradient: 50 μL of formic acid was added to 250 mL of water. Degas using an ultrasonic bath for 10 min.

Mobile phase B: Methanol Super Gradient.

Synthetic Procedures

Intermediate C-4A: 6-chloro-3-(3-methyl-2-oxobutylidene)-1H-indol-2-one

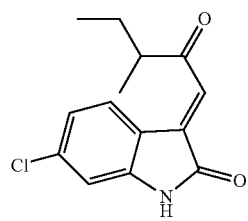 [SMILES: CCC(C)C(=O)/C=C1/C(=O)Nc2cc(Cl)ccc21]

A 5 L reaction vessel was charged with aldol C-3A (1015 g, 3.79 mol, 1 eq) and EtOH (2.85 L) was added. The suspension was heated to 55° C. and 12 M HCl (202 mL, 2.42 mol, 0.64 eq) was added in one portion. Then, heating was continued to boiling temperature of ethanol. It was found that more EtOH (500 mL) is needed because of product C-4A fast precipitation. After 1 h UPLCMS analysis showed 98% of the product peak area. The heating was stopped and cooling of the reaction mixture was started. When the temperature of the reaction mixture was reached 50° C., the whole mixture was transferred to a beaker and cooled to 0-5° C. The solid residue was filtered and washed with 1.3 L of cold EtOH. The solid product was dried in a laboratory drier (40° C.) for 3 h and then dried on air overnight. As a result, compound C-4A was obtained as an orange solid (692 g, 73% yield, 98.1% purity according to UPLCMS analysis).

Intermediate C-3A: 6-chloro-3-hydroxy-3-(3-methyl-2-oxobutyl)-2,3-dihydro-1H-indol-2-one

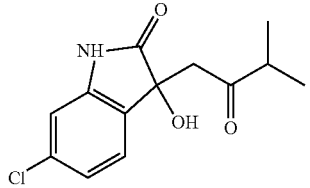 [SMILES: CC(C)C(=O)CC1(O)C(=O)Nc2cc(Cl)ccc21]

A 15 L reaction vessel was loaded with 6-chloroisatin (1000 g, 5.5 mol, 1 eq) and EtOH (7 L), and then 3-methylbutanone (2.94 L, 27.5 mol, 5 eq) was added in one portion. The reaction mixture was heated to 40° C. and DEA (250 mL, 2.41 mol, 0.44 eq) was added in one portion. Then, heating was continued to boiling temperature of ethanol. After 1 h UPLCMS analysis showed 71% of the product in the reaction mixture. The heating was continued for an additional 1 hour and after that time UPLCMS analysis showed 93% of the product. The reaction mixture was cooled to 50° C. and then the whole mixture was transferred to a round bottomed flask and all liquid ingredients were removed. The residue was suspended in DCM (3.4 L) and boiled under reflux for 1 h. After that time heating was stopped and n-hexane (2 L) was added in one portion. The flask content was cooled to around 5° C. and stirred for 1.5 h at this temperature. The resultant mixture was filtered and such obtained solid was washed with 500 mL of DCM/n-hexane (1:1) mixture followed by drying it on air overnight. As a result expected aldol product C-3A was obtained as a grey solid (965 g, 98.5% purity according to UPLCMS analysis). The solvent mixture after filtration was reduced in vacuo to around 1.5 L, n-hexane was added (700 mL) and obtained suspension was stirred for 0.5 h at room temperature. Another filtration followed by a double washing with DCM/n-hexane mixture (150 mL, 1:1, for each washing) and drying on air afforded second part of aldol product C-3A (50 g, 99.1% purity). The total yield of the aldol C-3A was 69% (1015 g, 98.5% purity according to UPLCMS analysis).

Intermediate C-4B: 6-chloro-3-(3-methyl-2-oxopentylidene)-2,3-dihydro-1H-indol-2-one

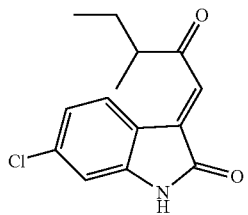 [SMILES: CCC(C)C(=O)/C=C1/C(=O)Nc2cc(Cl)ccc21]

A 250 mL reaction flask was charged with aldol C-3B (11 g, 39 mmol, 1 eq) and EtOH (32 mL) was added in one portion. The suspension was heated to 55° C. and 12 M HCl (1.63 mL, 19.5 mmol, 0.5 eq) was added in one portion. Then, heating was continued to boiling temperature of ethanol. After 1 h UPLCMS analysis showed 98% of the product. Reaction mixture was cooled to 0-5° C. and stirred for 0.5 h. The solid residue was filtered and washed with a small portion of cold EtOH. The solid product was dried on air overnight. As a result, compound C-4B was obtained as an orange solid (5 g, 49% yield, 99% purity according to UPLCMS analysis).

Intermediate C-3B: 6-chloro-3-hydroxy-3-(3-methyl-2-oxopentyl)-2,3-dihydro-1H-indol-2-one

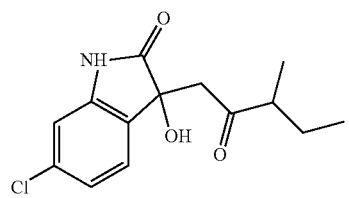 [SMILES: CCC(C)C(=O)CC1(O)C(=O)Nc2cc(Cl)ccc21]

In a round bottom flask (250 mL) 6-chloroisatin (15 g, 83 mmol, 1 eq) was suspended in EtOH (70 mL), and then 3-methylpent-2-one (51.3 mL, 415 mmol, 5 eq) was added in one portion. The reaction mixture was heated to 40° C. and DEA (4.34 mL, 42 mol, 0.5 eq) was added in one portion. Then, heating was continued to boiling temperature of ethanol. After 1 h UPLCMS analysis showed 60% of the product. The heating was continued for an additional 2 hours and after that time UPLCMS analysis showed 99% of the product. After cooling to room temperature all liquid ingredients were removed in vacuo. The residue was suspended in AcOEt (50 mL) and stirred at room temperature for 1 h. After that time the flask content was cooled to around 5° C. and stirred for 1.5 h at this temperature. The resultant mixture was filtered and such obtained solid was washed with a small amount of cold EtOH followed by drying it on air overnight. As a result, expected aldol product C-3B was obtained as a light brown solid (5.1 g, 98.5% purity according to UPLCMS analysis). The residue after filtration was preadsorbed onto silicagel and purified using flash chromatography (30% to 60% of AcOEt in n-hexane). After chromatography second part of product C-3B was obtained as a light brown solid (5.9 g) with 97% of purity (according to UPLCMS analysis). The total yield of the aldol C-3B was 47% (11 g, 98% purity according to UPLCMS analysis).

Intermediate C-6A: N-(3-chlorophenyl)prop-2-ynamide

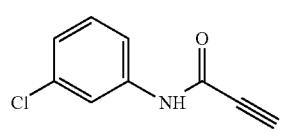

In a 2 L two-neck round-bottomed flask equipped with mechanical stirring, 3-chloroaniline (75 g, 590 mmol, 1 eq) was dissolved in 500 mL DCM (HPLC grade). Then, prop-2-ynoic acid (53.5 g, 760 mmol, 1.3 eq) dissolved in 100 mL DCM was added dropwise (the salt of the amine appeared). In the next step EDC.HCl (145 g, 760 mmol, 1.3 eq) was added in several portions (during the addition the reaction flask was cooled in an ice bath to avoid refluxing of the DCM). After full addition of EDC.HCl, the reaction mixture was stirred for 2 h at room temperature, and then the mixture was slowly transferred into the beaker containing 500 mL of water and 250 g of ice. Stirring was continued at 0-5° C. for around 15 min and then white precipitate was filtered off, washed with 100 mL of cold water and dried on air. As a result, expected amide C-6A was obtained as a white solid (102 g, 96.6% yield, 96.3% purity according to UPLCMS analysis).

Intermediate C-6B:
N-(5-chloro-2-fluorophenyl)prop-2-ynamide

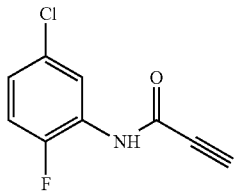

The prop-2-ynoic acid (15.16 g, 216.4 mmol, 1.05 eq) was added in one portion to a stirred solution of 5-chloro-2-fluoroaniline (30 g, 206.1 mmol, 1 eq) in toluene (400 mL) which was cooled in an ice/water bath. The mixture was stirred for 15 min, then DCC (44.65 g, 216.4 mmol, 1.05 eq) was added portionwise while maintaining the temperature below 10° C. Stirring was continued at 5° C. for 2 h, then solid DCU was collected by filtration, and washed with toluene (150 mL) and finally with mixture of AcOEt/n-hexane (150 mL, 1:9). The filtrate was concentrate to a volume of about 100 mL and stirred for 15 min at room temperature. The resulting precipitate was collected by filtration, washed with the mixture of toluene/n-hexane (20 mL, 1:1), n-hexane (20 mL) and air-dried for 16 h to give 15.29 g of the desired product as a white solid. The filtrate was placed in a refrigerator for 3 h and the resulting precipitate was collected by filtration, washed with the mixture of toluene/n-hexane (20 mL, 1:1), n-hexane (20 mL) and air-dried for 16 h to give 13.29 g of the amide C-6B. The filtrate was concentrated to a volume of approximately 20 mL and then hexane (400 mL) was slowly added while stirring. The mixture was refluxed for 30 min, and hot solution was filtered, concentrated to approximately 100 mL and placed in a refrigerator for 18 h. The resulting precipitate was collected by filtration, washed with n-hexane (2×20 mL) and air-dried for 16 h to give additionally 7.19 g of the amide C-6B. Total yield of the product C-B6 was 88% (35.77 g).

Intermediate C-6C:
N-(5-chloro-2-methylphenyl)prop-2-ynamide

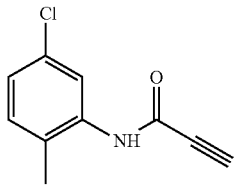

In a 2 L two-neck round-bottomed flask equipped with mechanical stirring, 5-chloro-2-methylaniline (75 g, 530 mmol, 1 eq) was dissolved in 1000 mL DCM (HPLC grade). Then, prop-2-ynoic acid (49 g, 690 mmol, 1.3 eq) dissolved in 100 mL DCM (HPLC grade) was added dropwise (the salt of the amine appeared). In the next step EDC.HCl was added in several portions (during the addition the reaction flask was cooled in an ice bath to avoid refluxing of the DCM). After full addition of EDC.HCl, the reaction mixture was stirred for 1 h at room temperature. The whole mixture was transferred to a beaker containing 750 mL of water and 250 g of ice. Stirring was continued at 0-5° C. for around 15 min and then white precipitate was filtered off, washed with 100 mL of cold water and dried on air. As a result, expected amide C-6C was obtained as a white solid (81 g, 80% yield, 99.1% purity according to UPLCMS analysis).

Intermediate C-6D:
N-(3-chloro-4-fluorophenyl)prop-2-ynamide

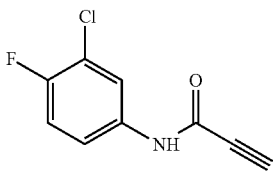

To a 1 L two-neck round-bottomed flask equipped with magnetic stirring bar and thermometer, 3-chloro-4-fluoroaniline (14.8 g, 100 mmol, 1 eq) was added followed by DCM (200 mL, HPLC grade) and prop-2-ynoic acid (9.1 g, 130 mmol, 1.3 eq). The reaction mixture was cooled to 0° C. and EDC.HCl (25.2 g, 130 mmol, 1.3 eq) was added in several portions. Reaction is exothermic and one should avoid exceeding +5° C. during the addition. After full addition of EDC.HCl, mixture was stirred for 1 h at the 5° C. After this time, an ice bath was removed and to the reaction mixture 200 mL of cold water was added. The reaction was stirred for around 0.5 h and the resulting precipitate was filtered off and washed with 100 mL of cold water. Thus obtained solid was redissolved in chloroform, and the solution was washed with water, dried over $Na_2SO_4$ and solvent was evaporated to dryness. The resulting product was dried in vacuo. As a result, expected amide C-6D was obtained as a light yellow solid (19.2 g, 98% yield, 98% purity according to UPLCMS analysis).

Intermediate C-6E:
N-(3,4-difluorophenyl)prop-2-ynamide

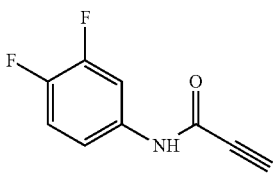

To a 1 L two-neck round-bottomed flask equipped with magnetic stirring bar and thermometer, 3,4-difluoroaniline (12.9 g, 9.9 mL, 100 mmol, 1 eq) was added followed by DCM (300 mL, HPLC grade) and prop-2-ynoic acid (9.1 g, 130 mmol, 1.3 eq). The reaction mixture was cooled to 0° C. and EDC.HCl (24.9 g, 130 mmol, 1.3 eq) was added in several portions. Reaction is exothermic and one should avoid exceeding +5° C. during the addition. After full addition of EDC.HCl, mixture was stirred for 1 h at the 5°

C. After this time, an ice bath was removed and to the reaction mixture 300 mL of cold water was added. The reaction was stirred for around 0.5 h and the resulting precipitate was filtered off and washed with 100 mL of cold water. Thus obtained solid was redissolved in AcOEt, and the solution was washed with water, dried over Na$_2$SO$_4$ and solvent was evaporated to dryness. Next the product was washed with 10 mL of cold DCM and dried in vacuo. As a result, expected amide C-6E was obtained as an off-white solid (17.3 g, 96% yield, 100% purity according to UPLCMS analysis).

Intermediate C-6F:
N-(5-chloro-2,4-difluorophenyl)prop-2-ynamide

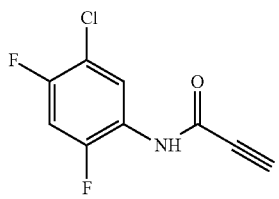

In a 500 mL two-neck round-bottomed flask equipped with magnetic stirrer, 5-chloro-2,4-difluoroaniline (10 g, 61 mmol, 1 eq) was dissolved in DCM (150 mL, HPLC grade). Then, prop-2-ynoic acid (5.5 g, 78 mmol, 1.3 eq) was added dropwise (the salt of the amine appeared). Next EDC.HCl (14 g, 78 mmol, 1.3 eq) was added in several portions (during the addition the reaction flask was cooled in an ice bath to maintain the room temperature. After full addition of EDC.HCl, the reaction mixture was stirred for an additional 1 h at room temperature. After that time 150 ml of water was added and the mixture was transferred into a separatory funnel. The phases were separated. The water phase was extracted twice with the DCM (2×100 mL). The organic fractions were combined, washed with brine, dried over MgSO$_4$ and concentrated to approximately 50 ml in vacuo, resulting a thick suspension. The solids were filtered and dried to furnish 8 g of cream crystals. The filtrate was concentrated and then purified by flash chromatography (n-hexane/AcOEt; 8:1→5:1) giving additional 4.4 g of the amide C-6F. As a result, expected amide C-6F was obtained as a cream solid (12.4 g, 94% yield, 100% purity according to UPLCMS analysis).

Intermediate C-7A:
5-amino-2,4-dimethoxypyrimidine

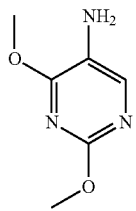

To a QianCap glass reactor (1850 mL) equipped with magnetic stirrer was added C-7A2 (100 g, 540 mmol) followed by THF (800 mL). Next, 10% palladium on carbon (2 g) was added in one portion and the reactor was connected to the source of the hydrogen. Hydrogen pressure was set at 2 bar and reaction was well stirred for 16 h under continuous flow of hydrogen. After that time, UPLCMS analysis has shown complete conversion of starting material. The reaction mixture was filtered through the Cellite pad and the filtrate was concentrated in vacuo to around 150-200 mL. Then, n-hexane (500 mL) was added dropwise and the suspension was stirred for 2 h at room temperature. The precipitate was filtered, washed twice with n-hexane (2×50 mL) and vacuum dried. As a result, amine C-7A was obtained as a yellow/green solid (77.94 g, 93% yield, 99% purity according to UPLCMS analysis).

Intermediate C-7A2:
2,4-dimethoxy-5-nitropyrimidine

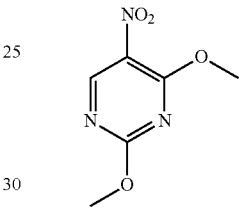

To a 2 L three-neck round-bottom flask, containing thermometer, water condenser, connection to inert gas source (argon) and mechanical stirrer, was added methanol (1 L, HPLC grade) and under argon atmosphere small pieces of sodium (65 g, 2.83 mol, 2.2 eq) were slowly added for around 1 h with well stirring (reaction is exothermic, but the reaction mixture was not cooled; usually another sodium piece was added when first was consumed). After dissolving the whole portion of sodium, reaction mixture was cooled to −5° C. and freshly prepared suspension of the C-7A1 (250 g, 1.29 mol, 1 eq) in methanol (500 mL, HPLC grade) was carefully added (around 40 minutes) in small portions with well stirring. (CAUTION: reaction is highly exothermic), one should avoid exceeding +10° C. during the addition. Moreover, in the course of the reaction lots of solid product was formed. After the whole amount of the substrate suspension was added, reaction mixture was maintained at 0-5° C. for around 0.5 h and then it was allowed to reach room temperature (usually it took around 2 h). After that time, UPLCMS analysis showed complete consumption of the substrate. Then, reaction mixture was cooled to around 5° C. and solid product was filtered, and washed with small amount (100 mL) of cold methanol. The crude product was placed in a beaker with water (1 L) and it was well suspended with mechanic stirrer (around 10 minutes of well stirring). The suspension was then filtered and obtained solid was washed with water (500 mL), n-hexane (200 mL) and dried on air overnight. As a result, 211.5 g of the compound C-7A2 was obtained as a light yellow solid (88% yield, 99% purity according to UPLCMS analysis).

Intermediate C-7B: 5-amino-2,4-dimethoxypyridine

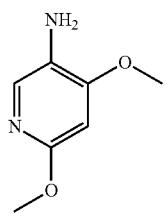

To a QianCap glass reactor (1850 mL) equipped with magnetic stirrer was added C-7B2 (40 g, 217 mmol) followed by THE (500 mL). Next, 10% palladium on carbon (1.5 g) was added in one portion and the reactor was connected to the source of the hydrogen. Hydrogen pressure was set at 2 bar and reaction was well stirred for 7 h under continuous flow of hydrogen. After that time, UPLCMS analysis showed complete conversion of starting material. The reaction mixture was filtered through the Cellite pad and the filtrate was concentrated in vacuo. As a result, amine C-7B was obtained as a brown solid (33 g, 99% yield).

Intermediate C-7B2: 2,4-dimethoxy-5-nitropyridine

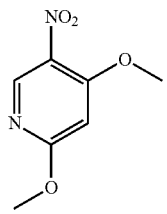

To a 2 L three-neck round-bottom flask, containing thermometer, water condenser, connection to inert gas source (argon) and mechanical stirrer, was added methanol (900 mL, HPLC grade) and under argon atmosphere small pieces of sodium (26.7 g, 1.16 mol, 2.1 eq) were slowly added for around 1 h with well stirring (CAUTION: reaction is exothermic, but the reaction mixture was not cooled; usually another sodium piece was added when first was consumed). After dissolving the whole portion of sodium, reaction mixture was cooled to −5° C. and freshly prepared suspension of the compound C-7B1 (106.25 g, 0.55 mol, 1 eq) in methanol (100 mL, HPLC grade) was carefully added (around 30 minutes) in small portions with well stirring (CAUTION: reaction is highly exothermic, one should avoid exceeding +10° C. during the addition). After the whole amount of the substrate C-7B1 suspension was added, reaction mixture was maintained at 0-5° C. for around 40 min and then it was warmed to room temperature and stirred at 40° C. for 3.5 h. After that time, UPLCMS analysis showed complete consumption of the substrate. Then, the reaction mixture was cooled below 10° C. and the solid product was filtered and washed with a small amount (50 mL) of cold methanol, water (100 mL), n-hexane (100 mL) and dried on air overnight. In result, 99.3 g of the compound C-7B2 was obtained as a light yellow solid (98% yield, 97% purity according to UPLCMS analysis).

Intermediate C-7C: 5-amino-4-methoxy-2-(dimethylamino)pyridine

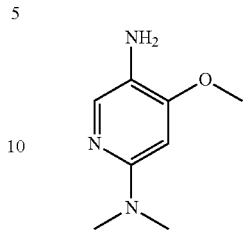

To a QianCap glass reactor (500 mL) equipped with magnetic stirrer was added C-7C$_2$ (4.5 g, 22.8 mol) followed by THE (70 mL) and methanol (70 mL). Next, 10% palladium on carbon (0.48 g) was added in one portion, the reactor was connected to the source of the hydrogen. Hydrogen pressure was set at 2 bar and reaction was well for 17 h under continuous flow of hydrogen at room temperature. After that time UPLCMS analysis showed complete conversion of the starting material. The reaction mixture was filtered through the Cellite pad and the filtrate was concentrated in vacuo to dryness. As a result, amine C-7C was obtained as a dark solid (3.9 g; 96% yield; 95% purity according to UPLCMS analysis).

Intermediate C-7C2: 4-methoxy-2-(dimethylamino)-5-nitropyridine

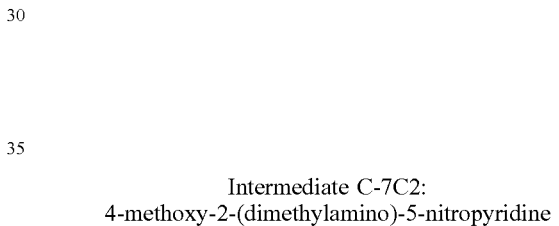

A 0.5 L three-neck round-bottom flask, containing thermometer, water condenser and dropping funnel were charged with C-7C1 (10 g, 50.4 mmol, 1 eq), THF (50 mL) and methanol (200 mL). The whole mixture was stirred at 22° C. for 10 min and then dimethylamine (13.7 mL, 60% solution in water) was added dropwise. After 1 h a pale yellow solid started to precipitate. The next portion of dimethylamine (2 mL, 60% solution in water) was added and the reaction was continued for an additional 24 h. After that time the reaction mixture was concentrated in vacuo and the crude material was suspended in methanol (70 mL) and water (140 mL). After vigorous stirring for 1 h at 0° C. the pale yellow solid was filtered off, washed with a small amount of methanol-water solution and vacuum dried. As a result, compound C-7C2 was obtained as a pale yellow solid (10 g; 100% yield 99% purity according to UPLCMS analysis).

Intermediate C-7D:
5-amino-2,4,6-trimethoxypyrimidine

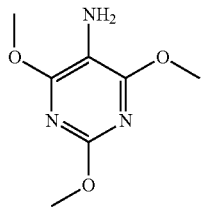

To a QianCap glass reactor (1850 mL) equipped with magnetic stirrer was added C-7D3 (46 g, 231 mmol) followed by MeOH (750 mL). Next, 10% palladium on carbon (2.5 g) was added in one portion and the reactor was connected to the source of the hydrogen. The hydrogen pressure was set at 2 bar and reaction was well stirred for 24 h under continuous flow of hydrogen. After that time, TLC analysis showed complete conversion of the starting material. The reaction mixture was filtered through the Cellite pad and the filtrate was concentrated in vacuo to dryness. As a result, amine C-7D was obtained as a beige solid (38.3 g, 97% yield, 99% purity according to UPLCMS analysis).

Intermediate C-7D3:
2,4,6-trimethoxy-5-nitropyrimidine

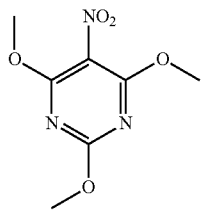

A methanol (1000 mL) was added to a 2 L round bottom flask containing a thermometer and a magnetic stirrer and the whole was cooled to 0° C. in a water/ice bath. Then sodium hydride (13 g, 327 mmol, 1.2 eq, 60% in mineral oil) was added in small portions for 30 minutes (CAUTION: The reaction is exothermic). After 30 minutes of stirring the substrate C-7D2 (60 g, 272 mmol, 1 eq) was added in several portions. The reaction is highly exothermic and during the addition the reaction flask was cooled in a water/ice bath. During the reaction the formation of a solid yellow product was observed. The reaction mixture was allowed to reach room temperature (1 h) and after that time TLC analysis (DCM as an eluent) showed complete conversion of the starting material. To the reaction mixture 1 L of water was added and methanol was evaporated. The precipitate was filtered off, washed with 200 mL of n-hexane and dried on air. As a result, compound C-7D3 was obtained as a yellow solid (46.5 g, 79% yield, 100% purity according to UPLCMS analysis).

Intermediate C-7D2:
2-chloro-4,6-dimethoxy-5-nitropyrimidine

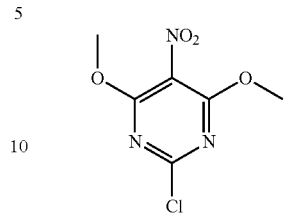

To a 0.5 L two-neck round-bottom flask, containing thermometer and equipped with magnetic stirrer was added the compound C-7D1 (50 g, 286 mmol, 1 eq) followed by addition of TFAA (80 mL, 572 mmol, 2 eq)/DCM mixture (1:1). The mixture was then cooled in a brine-ice bath to −5° C. Concentrated fuming nitric acid (14.3 mL, 343 mmol, 1.2 eq) was added drop-wise to the well stirred mixture (CAUTION: Reaction is highly exothermic) at such to not exceed +40° C. In the course of the reaction lots of solid product was formed. After the whole amount of the nitric acid was added, reaction mixture was allowed to reach room temperature. After that time, TLC analysis showed complete consumption of the substrate (an aliquot which was quenched with water and extracted with DCM; plate eluted with DCM). The resulting thick white precipitate was poured onto ice and the stirring was continued for 10 minutes. The aqueous solution was extracted with DCM (3×100 mL). The combined organic layers were then washed with saturated aqueous NaHCO$_3$ solution until the washings remained at pH 7. The solution was dried over MgSO$_4$ and the solvent was removed in vacuo to give a yellow-white crystalline compound C-7D2 (61 g, 97% yield, 99% purity according to UPLCMS analysis).

Compound (1), C1: (3S)-6-chloro-2'-(3-chlorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

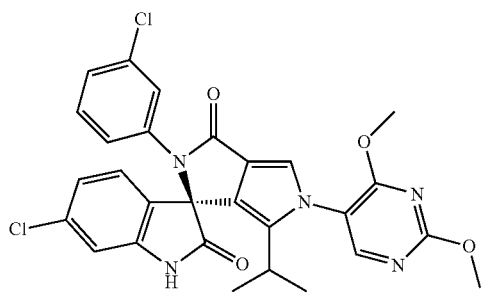 [SMILES: COc1ncc(-n2cc3c(c2C(C)C)[C@@]2(C(=O)Nc4cc(Cl)ccc42)N(c2cccc(Cl)c2)C3=O)c(OC)n1]

The title compound was obtained after preparative chiral SFC (method A) or chiral RP-HPLC separation (method R) of the racemic compound C-10.C1; >99% ee; t$_r$: 7.77 min. (method R'); $^1$H NMR (500 MHz, DMSO-d$_6$) δ 11.18 (s, 1H), 8.55-8.42 (m, 1H), 7.37 (s, 1H), 7.36-7.27 (m, 2H), 7.14 (s, 1H), 7.08 (dd, J=8.1, 1.9 Hz, 1H), 6.98 (d, J=7.8 Hz, 1H), 6.93 (d, J=1.9 Hz, 1H), 3.98 (s, 3H), 3.94 (s, 3H), 2.43 (sep, J=7.0 Hz, 1H), 0.86 (d, J=7.0 Hz, 3H), 0.43 (d, J=7.0 Hz, 3H); $^{13}$C NMR (126 MHz, DMSO-d$_6$) δ 175.42, 166.58, 164.87, 164.85, 157.89, 144.17, 138.80, 135.26, 134.00, 133.38, 130.76, 127.52, 127.42, 127.30, 126.96, 126.02, 123.70, 123.04, 120.65, 118.41, 116.45, 111.18, 70.20, 55.52, 54.85, 25.47, 21.41, 21.25.

Compound C-10.C1: 6-chloro-2'-3-chlorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

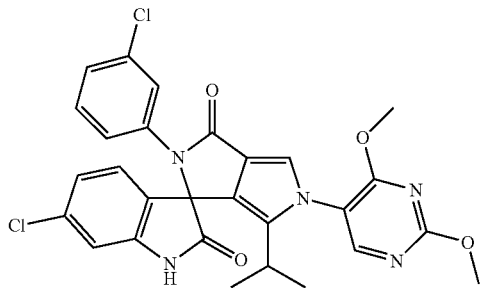 [SMILES: COc1ncc(-n2cc3c(c2C(C)C)C2(C(=O)Nc4cc(Cl)ccc42)N(c2cccc(Cl)c2)C3=O)c(OC)n1]

50 mL of TFA was placed in a 100 mL flask equipped with magnetic stirring bar. Then, intermediate C-9.C1 (17.8 g, 30.6 mmol) was added in several portions and the reaction mixture was vigorously stirred for 3 h at 40° C. After that time UPLCMS analysis showed 89% of product peak with some minor peaks from impurities. Most of the acid was then evaporated and the residue was dissolved in DCM (100 mL). 100 mL of water was added, and the mixture was treated with 3 M NaOH to pH 8. The phases were separated and the water phase was extracted with DCM (2×100 mL). The combined organic phases were washed with brine (30 mL), dried over $MgSO_4$ and evaporated to dryness to furnish 18 g of a beige solid compound C-10.C1 with 90% purity. The crude product C-10.C1 was dissolved in 50 mL of methanol (HPLC grade). Then, 25% solution of sodium methoxide (10 mL) was added dropwise within 10 minutes and the mixture was stirred at room temperature. After 24 h UPLCMS analysis showed 97% of the expected product C-10.C1. The mixture was concentrated to half volume and transferred slowly to a stirred mixture of ice (100 g) and then acidified 3 M HCl to neutral pH. The precipitate was filtered off, rinsed with 50 mL of water and dried in vacuo to give compound C-10.C1 as a beige-orange solid (14.5 g, 84% yield, 98% purity according UPLCMS analysis).

Alternative Procedure for Preparation C-10.C1

12.0 g (19 mmol) of Intermediate C-9.C1 was dissolved in 50 mL of glacial AcOH. MsOH (1 eq) was added and the mixture was stirred at 40° C. After 16 hours, the mixture was transferred to a beaker containing 100 g of ice and 100 mL of 25% ammonia. The solid product was filtered, rinsed with 50 mL water and dried on air. Purification by flash chromatography (DCM/MeOH, 100:0→98:2) resulted in 9.6 g of a beige-orange solid with 94% purity (according UPLCMS analysis). Yield: 78%.

Compound C-9.C1: 4-(6-chloro-3-hydroxy-2-oxo-2,3-dihydro-1H-indol-3-yl)-N-(3-chlorophenyl)-1-(2,4-dimethoxypyrimidin-5-yl)-5-(propan-2-yl)-1H-pyrrole-3-carboxamide

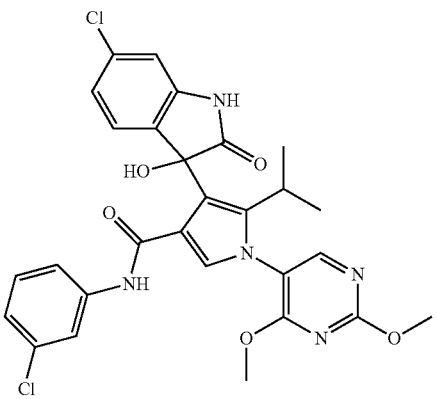 [SMILES: COc1ncc(-n2cc(C(=O)Nc3cccc(Cl)c3)c(C3(O)C(=O)Nc4cc(Cl)ccc43)c2C(C)C)c(OC)n1]

To a 500 mL flask equipped with magnetic stirring bar, compound C-8.C1 (15 g, 26.6 mmol, 1 eq) and THF (200 mL) were added followed by triethyl phosphite (6.81 mL, 39.8 mmol, 1.5 eq). Then, sodium tert-butoxide (5.11 g, 53.2 mmol, 2 eq) was added in several portions. The reaction mixture was stirred for 3 h at room temperature under the air atmosphere (the flask was equipped with $CaCl_2$) tube). After that time UPLCMS analysis showed 82% of the desired product and 10% of main impurity. The reaction mixture was slowly transferred into a chilled (0-5° C.) mixture of water (150 mL) and 12 M HCl (5 mL). After addition of AcOEt (100 mL) the whole mixture was transferred into a separatory funnel. Layers were separated and the water phase was extracted once again with AcOEt (100 mL). Combined organic phases were washed with brine, dried over $MgSO_4$ and the solvent was removed in vacuo. The crude products was purified using flash chromatography ($CHCl_3$/MeOH 100:0→98:2). As a result, 5.86 g of C-9.C1 was obtained with 93.7% purity. Yield: 38%.

Compound C-8.C1: 4-(6-chloro-2-oxo-2,3-dihydro-1H-indol-3-yl)-N-(3-chlorophenyl)-1-(2,4-dimethoxypyrimidin-5-yl)-5-(propan-2-yl)-1H-pyrrole-3-carboxamide

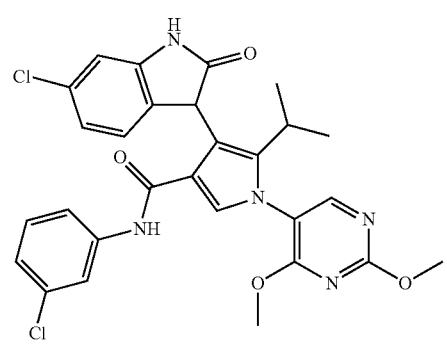 [SMILES: COc1ncc(-n2cc(C(=O)Nc3cccc(Cl)c3)c(C3C(=O)Nc4cc(Cl)ccc43)c2C(C)C)c(OC)n1]

In a 500 mL round-bottomed flask equipped with magnetic stirring bar, compounds C-4A (21 g, 117 mmol, 1 eq), C-6A (29.25 g, 117 mmol, 1 eq) and C-7A (20 g, 130 mmol, 1.1 eq) were suspended in 90% aqueous AcOH, and the flask was tightly closed with plastic stopper. The mixture was heated up to 70° C. and stirred at this temperature for 24 h. After that time UPLCMS analysis showed 60% of the expected product. The reaction mixture was cooled to room temperature and evaporated to dryness. The reaction was repeated and the residue from two batches were combined and purified according to the following procedure:

The solid residue was preadsorbed onto silicagel and purified using flash chromatography (30% to 50% of AcOEt in n-hexane). All fractions which contained the product were concentrated to 500 mL and left at the room temperature. After 24 hours the pink solid was filtered off, rinsed with 50 mL of n-hexane and dried on air (40.8 g, 96.5% purity according to UPLCMS analysis). The filtrate was evaporated to dryness to furnish additional 6.6 g of product C-8.C1, with 50% purity. Yield: 33%.

Compound (2), C2: (3S)-6-chloro-2'-(5-chloro-2-fluorophenyl)-5'-(2,4-dimethoxypyrimidin-5-yl)-6'-(propan-2-yl)-1,2,3',5'-tetrahydro-2'H-spiro[indole-3, 1'-pyrrolo[3,4-c]pyrrole]-2,3'-dione

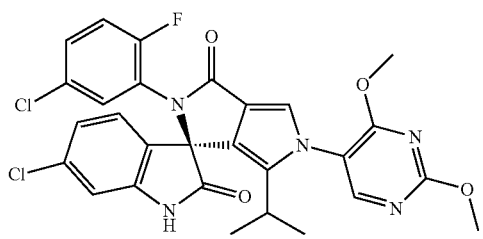 [SMILES: COc1ncc(-n2cc3c(c2C(C)C)[C@@]2(C(=O)Nc4cc(Cl)ccc42)N(c2cc(Cl)ccc2F)C3=O)c(OC)n1]

The title compound was obtained after preparative chiral SFC (method B) or chiral RP-HPLC (method N) separation of the racemic compound C-10.C2; >99% ee; $t_r$: 9.31 min. (method N'); $^1$H NMR (500 MHz, DMSO-$d_6$) δ 11.23 (br s, 1H), 8.50 (br s, 1H), 7.45 (ddd, J=8.9, 4.1, 2.7 Hz, 1H), 7.39 (s, 1H), 7.32 (t, J=9.1 Hz, 1H), 7.21-7.13 (m, 1H), 7.08 (dd, J=8.1, 1.9 Hz, 1H), 7.05 (dd, J=6.3, 2.7 Hz, 1H), 6.90 (d, J=1.9 Hz, 1H), 3.98 (s, 3H), 3.94 (br s, 3H), 2.48-2.39 (m, 1H), 0.85 (d, J=7.0 Hz, 3H), 0.44 (d, J=7.0 Hz, 3H); $^{13}$C NMR (125 MHz, DMSO-$d_6$) δ 175.51, 166.44, 164.70, 164.24, 158.75, 157.96, 156.74, 144.03, 135.39, 134.14, 130.82, 130.75, 129.58, 128.33, 127.30, 125.99, 125.66, 125.54, 123.64, 123.04, 119.63, 118.75, 118.68, 118.57, 116.25, 111.12, 70.04, 55.67, 55.01, 49.04, 25.34, 22.00, 21.50-20.80.

Compound C-10.C2: 6-chloro-2'-(5-chloro-2-fluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

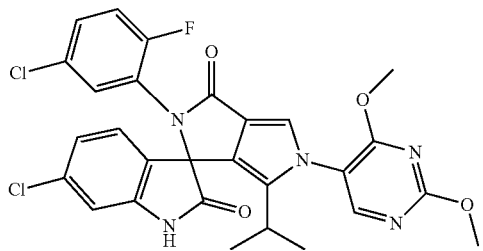 [SMILES: COc1ncc(-n2cc3c(c2C(C)C)C2(C(=O)Nc4cc(Cl)ccc42)N(c2cc(Cl)ccc2F)C3=O)c(OC)n1]

To a 100 mL flask equipped with magnetic stirring bar, compound C-9.C2 (2.86 g, 4.76 mmol) was added and the flask was cooled on an ice bath. Then, TFA (25 mL) was added (around 2 mL/min). The cooling bath was removed and the reaction was stirred for 2 h at room temperature. After that time UPLCMS analysis showed 72% of product peak area The mixture was then poured into ice (around 100 g) and diluted with DCM (50 mL). The phases were separated and the water phase was extracted with DCM three times. The combined organic phases were washed with water and brine and solvent was removed in vacuo. The crude mixture was preadsorbed onto silicagel and purified using flash chromatography (AcOEt/hexane 40%→60%). The brown solid obtained after chromatography (1.51 g) was stirred in 60% AcOEt in n-hexane (10 mL) for 0.5 h and then filtered, washed with 60% AcOEt in n-hexane and dried on air. In result, compound C-10.C2 was obtained as a light brown solid (1.35 g, 46% yield) with 96% of purity according to UPLCMS analysis.

Compound C-9.C2: N-(5-chloro-2-fluorophenyl)-4-(6-chloro-3-hydroxy-2-oxo-2,3-dihydro-1H-indol-3-yl)-1-(2,4-dimethoxypyrimidin-5-yl)-5-(propan-2-yl)-1H-pyrrole-3-carboxamide

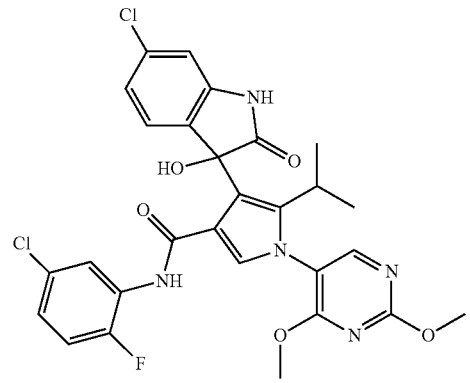 [SMILES: COc1ncc(-n2cc(C(=O)Nc3cc(Cl)ccc3F)c(C3(O)C(=O)Nc4cc(Cl)ccc43)c2C(C)C)c(OC)n1]

To a 500 mL flask equipped with magnetic stirring bar, compound C-8.C2 (5 g, 8.6 mmol, 1 eq) and THF (80 mL) were added followed by trimethyl phosphite (2 mL, 17.2 mmol, 2 eq). Then, reaction mixture was cooled in an ice bath and sodium tert-pentoxide (3.79 g, 344 mmol, 4 eq) was added in one portion. Cooling bath was removed and reaction was stirred for 1 h at room temperature (the flask was equipped with CaCl$_2$ tube). After that time UPLCMS analysis showed 91% of the product peak area. Around 90% of the solvent was removed and such obtained mixture was diluted with 100 mL of water. The resulting suspension was acidified with 3 M HCl to pH ~5 and diluted with 100 mL of DCM. The phases were separated and the water phase was extracted with DCM three times. The combined organic phases were washed with water, brine, dried over Na$_2$SO$_4$ and solvent was removed in vacuo. The crude product C-9.C2 was obtained as a red-brown solid/foam (72% purity according to UPLCMS analysis) and was used in the next step without any further purification.

Compound C-8.C2: N-(5-chloro-2-fluorophenyl)-4-(6-chloro-2-oxo-2,3-dihydro-1H-indol-3-yl)-1-(2,4-dimethoxypyrimidin-5-yl)-5-(propan-2-yl)-1H-Pyrrole-3-carboxamide

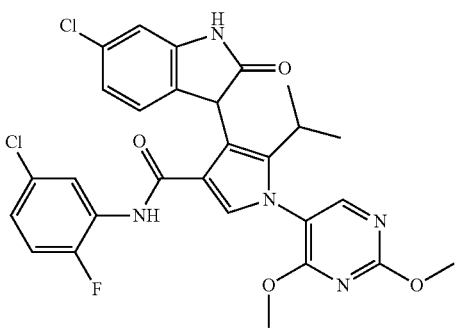 [SMILES: COc1ncc(-n2cc(C(=O)Nc3cc(Cl)ccc3F)c(C3C(=O)Nc4cc(Cl)ccc43)c2C(C)C)c(OC)n1]

To a 500 mL flask equipped with magnetic stirring bar, compounds C-4A (12.48 g, 50 mmol, 1 eq), C-7A (7.76 g, 50 mmol, 1 eq) and C-6B (9.88 g, 50 mmol, 1 eq) were added followed by glacial AcOH (125 mL), and the flask was tightly closed with plastic stopper. The mixture was heated up to 90° C. (temperature of the heating bath) and stirred at this temperature for 16 h. After that time UPLCMS analysis showed almost full consumption of starting materials (which equals to 40% of a product peak area). The reaction mixture was cooled to room temperature and AcOH was evaporated to dryness. The residue was preadsorbed onto silicagel and purified using flash chromatography (30% to 60% of AcOEt in n-hexane). After removing of solvents product C-8.C2 was obtained as a dark red solid/foam (8.7 g, 30% yield) with 84% of purity according to UPLCMS analysis.

Compound (3), C3: (3S)-6-chloro-2'-(5-chloro-2-methylphenyl)-6'-(propan-2-yl)-5'-(trimethoxypyrimidin-5-yl)-1,2,3',5'-tetrahydro-2'H-spiro[indole-3,1'-pyrrolo[3,4-c]pyrrole]-2,3'-dione

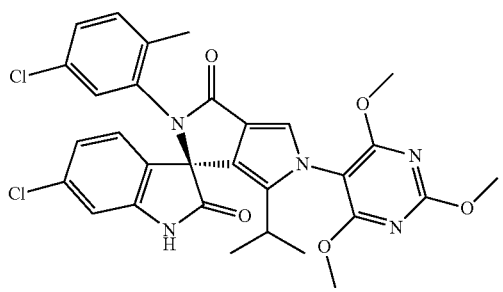 [SMILES: COc1nc(OC)c(-n2cc3c(c2C(C)C)[C@@]2(C(=O)Nc4cc(Cl)ccc42)N(c2cc(Cl)ccc2C)C3=O)c(OC)n1]

The title compound was obtained after preparative chiral SFC (method C) or chiral RP-HPLC (method T) separation of the racemic compound C-10.C3; >99% ee; t$_r$: 16.7 min (method T'). $^1$H NMR (600 MHz, DMSO-d) mixture of rotamers: δ 11.31 (br s, 1H), 10.90 (br s, 1H), 7.35 (d, J=8.1 Hz, 1H), 7.33-7.18 (m, 4H), 7.02 (dd, J=8.1, 2.0 Hz, 1H), 6.91 (d, J=1.9 Hz, 1H), 6.86 (d, J=1.9 Hz, 1H), 6.44 (d, J=2.2 Hz, 1H), 3.97 (d, J=1.4 Hz, 3H), 3.93 (d, J=4.3 Hz, 3H), 3.90 (d, J=2.4 Hz, 3H), 2.38-2.32 (m, 1H), 2.24 (s, 1H), 2.07 (s, 2H), 0.80 (dd, J=13.5, 7.0 Hz, 3H), 0.41 (dd, J=10.0, 7.0 Hz, 3H); $^{13}$C NMR (151 MHz, DMSO-d$_6$) mixture of rotamers: δ 176.16, 174.19, 167.19, 167.05, 166.99, 166.89, 163.67, 163.37, 162.67, 143.81, 137.44, 136.75, 136.68, 136.17, 134.82, 134.74, 133.24, 133.19, 132.37, 132.31, 129.95, 129.22, 128.11, 127.96, 127.92, 127.45, 127.11, 127.05, 125.63, 122.64, 122.44, 122.19, 119.53, 119.28, 117.89, 110.67, 110.59, 99.16, 70.13, 69.70, 55.04, 54.78, 54.74, 54.71, 40.41, 40.03, 39.89, 24.99, 24.97, 21.84, 21.06, 21.02, 20.85, 20.78, 17.97, 17.82.

Compound C-10.C3; 6-chloro-2'-(5-chloro-2-methylphenyl)-6'-(propan-2-yl)-5'-(trimethoxypyrimidin-5-yl)-1,2,3',5'-tetrahydro-2'H-spiro[indole-3,1'-pyrrolo[3,4-c]pyrrole]-2,3'-dione

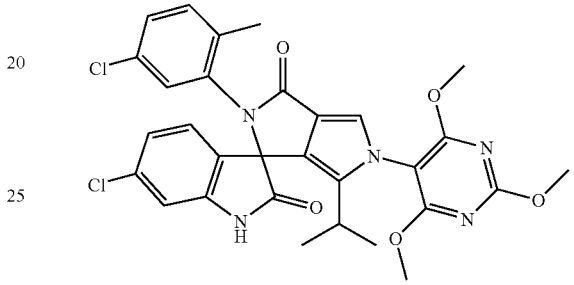

To a 25 mL flask equipped with magnetic stirring bar, compound C-9.C3 (6.7 g, 1.19 mmol) and AcOH (10 mL) were added at room temperature. Then MsOH (0.077 mL. 1.19 mmol) was added and the reaction mixture was stirred for 3 h at 80° C. After 1 h UPLCMS analysis showed 93% of product peak area. AcOH was evaporated and the residue was dissolved in AcOEt, washed with saturated NaHCO$_3$, brine and dried over MgSO$_4$. The mixture was concentrated to around 5 mL of AcOEt, and the suspension was filtered. Collected solid was washed with 5 mL of AcOEt and dried in vacuo. The desired product C-10.C3 was obtained as a white solid (0.31 g, 43% yield, 98% purity according to UPLCMS analysis).

Compound C-9.C3: N-(5-chloro-2-methylphenyl)-4-(6-chloro-3-hydroxy-2-oxo-2,3-dihydro-1H-indol-3-yl)-5-(propan-2-yl)-1-(trimethoxypyrimidin-5-yl)-1H-pyrrole-3-carboxamide

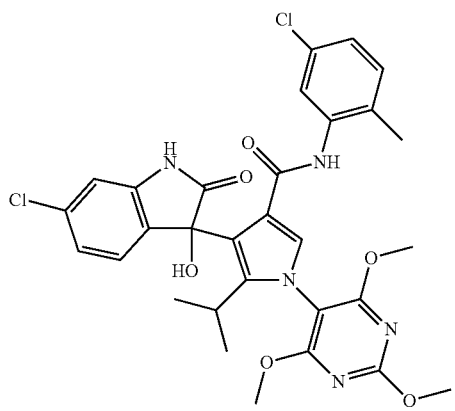 [SMILES: COc1nc(OC)c(-n2cc(C(=O)Nc3cc(Cl)ccc3C)c(C3(O)C(=O)Nc4cc(Cl)ccc43)c2C(C)C)c(OC)n1]

To a 50 mL flask equipped with magnetic stirring bar, compound C-8.C3 (0.8 g, 1.3 mmol, 1 eq) and THF (15 mL) were added. Then reaction mixture was cooled in an ice bath to 0° C. and triethyl phosphite (0.45 mL, 2.6 mmol, 2 eq) was added. After 10 minutes in 0° C. sodium tert-pentoxide (0.6 g, 5.2 mmol, 4 eq) was added in several portions. The reaction mixture was stirred at room temperature (the flask was equipped with CaCl$_2$ tube) and monitored by TLC (5% MeOH in CHCl$_3$). After 24 h the mixture was poured on ice and reaction was acidified with 1 M HCl to pH ~5. After addition of AcOEt (50 mL) the mixture was transferred into a separatory funnel. The layers were separated and the water phase was extracted once again with AcOEt (25 mL). The combined organic phases were washed with brine, dried over Na$_2$SO$_4$ and solvent was removed in vacuo. The residue was purified by column chromatography using 1% MeOH in CHCl$_3$ as an eluent. The desired product C-9.C3 was obtained as a pink solid (0.8 g, 90% yield, 93% purity according to UPLCMS analysis).

Compound C-8.C3: N-(5-chloro-2-methylphenyl)-4-(6-chloro-2-oxo-2,3-dihydro-1H-indol-3-yl)-5-(propan-2-yl)-1-(trimethoxypyrimidin-5-yl)-1H-pyrrole-3-carboxamide

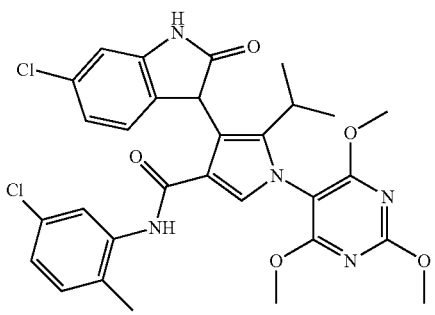 [SMILES: COc1nc(OC)c(-n2cc(C(=O)Nc3cc(Cl)ccc3C)c(C3C(=O)Nc4cc(Cl)ccc43)c2C(C)C)c(OC)n1]

In a 25 mL round-bottomed flask equipped with magnetic stirring bar, compounds C-4A (0.67 g, 2.7 mmol, 1 eq), C-7D (0.5 g, 2.7 mmol, 1 eq) and C-6C (0.52 g, 2.7 mmol, 1 eq) were added followed by glacial AcOH (10 mL), and the flask was tightly closed to with plastic stopper. The mixture was heated up to 90° C. and stirred at this temperature overnight. After that time UPLCMS analysis showed almost full consumption of starting materials (which equals to 45% of a product peak area). AcOH was then evaporated in vacuo. The residue was purified by flash chromatography (n-hexane/AcOEt, 4:1→1:1) giving the expected product C-8.C3 as a red solid (0.8 g, 40% yield, 82% purity according to UPLCMS analysis).

Compound (4), C4: (3S)-6-chloro-2'-(3-chloro-4-fluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

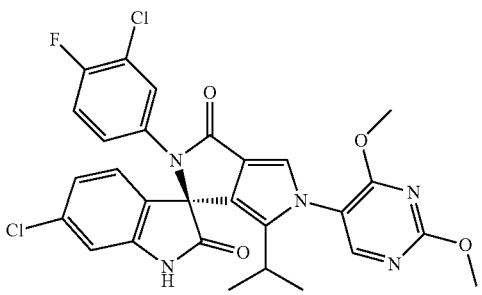 [SMILES: COc1ncc(-n2cc3c(c2C(C)C)[C@@]2(C(=O)Nc4cc(Cl)ccc42)N(c2ccc(F)c(Cl)c2)C3=O)c(OC)n1]

The title compound was obtained after preparative chiral SFC (method D) or chiral RP-HPLC (method K) separation of the racemic compound C-10.C4; >99% ee; t$_r$: 3.79 min (method K). $^1$H NMR (500 MHz, CDCl$_3$) δ 8.47 (br s, 1H), 8.23 (s, 1H), 7.24-7.19 (m, 1H), 7.18-7.12 (m, 1H), 7.12-7.06 (m, 1H), 7.05-6.96 (m, 2H), 6.96-6.86 (m, 2H), 4.07 (s, 3H), 3.99 (s, 3H), 2.49-2.38 (m, 1H), 0.90 (d, J=7.0 Hz, 3H), 0.52 (d, J=7.0 Hz, 3H); $^{13}$C NMR (125 MHz, CDCl$_3$) δ 175.2, 166.5, 165.6, 164.9, 158.5, 157.0, 156.5, 142.0, 136.4, 134.3, 132.6, 132.5, 131.0, 128.6, 128.5, 126.5, 126.2, 123.8, 122.8, 121.4, 121.3, 120.7, 117.8, 117.0, 116.8, 116.2, 111.6, 70.1, 55.6, 54.7, 25.6, 21.2, 1.9.

Compound C-10.C4; 6-chloro-2'-(3-chloro-4-fluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

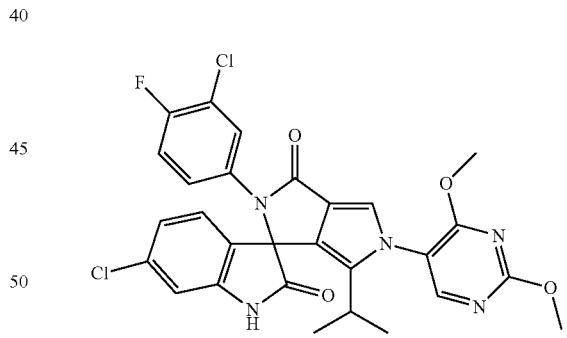

To a 250 mL flask equipped with magnetic stirring bar, compound C-9.C4 (10.34 mmol) and TFA (70 mL) were added at room temperature (TFA was added around 5 mL/min). Then, the reaction was stirred for 3 h at 40° C. and monitored by TLC. After this time UPLCMS analysis showed 71% of product peak area. The mixture was cooled to room temperature and evaporated to dryness. The crude product was purified by column chromatography (10%-50% AcOEt/n-hexane). After removing of solvents product C-10.C4 was obtained as a light brown solid/foam (5.44 g, 80% yield after two steps, starting from C-8.C4) with 88% of purity according to UPLCMS analysis.

Compound C-9.C4: 4-(6-chloro-3-hydroxy-2-oxo-2,3-dihydro-1H-indol-3-yl)-N-(3-chloro-4-fluorophenyl)-1-(2,4-dimethoxypyrimidin-5-yl)-5-(propan-2-yl)-1H-pyrrole-3-carboxamide

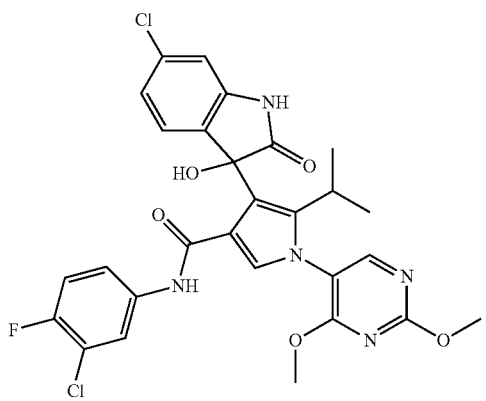 [SMILES: COc1ncc(-n2cc(C(=O)Nc3ccc(F)c(Cl)c3)c(C3(O)C(=O)Nc4cc(Cl)ccc43)c2C(C)C)c(OC)n1]

To a 500 mL flask equipped with magnetic stirring bar, compound C-8.C4 (6.04 g, 10.34 mmol, 1 eq) and THF (140 mL) were added. Then, reaction mixture was cooled in an ice bath to 0° C. and trimethyl phosphite (1.83 mL, 15.51 mmol, 1.5 eq), sodium tert-pentoxide (2.28 g, 20.68 mmol, 2 eq) were added in one portion. The reaction mixture was stirred for 4 h at this temperature (the flask was equipped with CaCl$_2$ tube) and monitored by TLC. After that time UPLCMS analysis showed 87% of the desired product peak area. Next, to the mixture was added cold water (50 mL) and reaction was acidified with 5% HCl to pH ~5. The reaction mixture was stirred for around 0.5 h at room temperature and the resulting precipitate was filtered off, washed with 100 mL of cold water. Thus obtained solid was redissolved in AcOEt, washed with water, dried over Na$_2$SO$_4$ and solvent was evaporated. The crude product C-9.C4 was obtained as a brown solid (85% purity according to UPLCMS analysis) and was used in the next step without any further purification.

Compound C-8.C4: 4-(6-chloro-2-oxo-2,3-dihydro-1H-indol-3-yl)-N-(3-chloro-4-fluorophenyl)-1-(2,4-dimethoxypyrimidin-5-yl)-5-(propan-2-yl)-1H-pyrrole-3-carboxamide

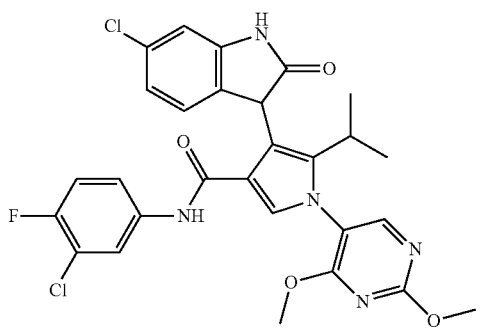 [SMILES: COc1ncc(-n2cc(C(=O)Nc3ccc(F)c(Cl)c3)c(C3C(=O)Nc4cc(Cl)ccc43)c2C(C)C)c(OC)n1]

To a 250 mL microwave reactor equipped with magnetic stirring bar, compounds C-4A (12.48 g, 50 mmol, 1 eq), C-7A (8.5 g, 55 mmol, 1.1 eq) and C-6D (9.9 g, 50 mmol, 1 eq) were added followed by glacial AcOH, and the MW reactor was tightly closed. The mixture was heated up to 90° C. (300 Watt) and stirred for 5 h at this temperature. After this time UPLCMS analysis showed almost full consumption of starting materials (which equals to 40% of a product peak area). Reaction mixture was cooled to room temperature and AcOH was evaporated to dryness. The residue was preadsorbed onto silicagel and purified by column chromatography (10% of acetone/DCM). After removing of solvents product C-8.C4 was obtained as a dark brown solid/foam (6.96 g, 20.7% yield) with 87% of purity according to UPLCMS analysis.

Compound (5), C5: (3S)-6-chloro-2'-(5-chloro-2-fluorophenyl)-6'-(propan-2-yl)-5'-(trimethoxypyrimidin-5-yl)-1,2,3',5'-tetrahydro-2'H-spiro[indole-3,1'-pyrrolo[3,4-c]pyrrole]-2,3'-dione

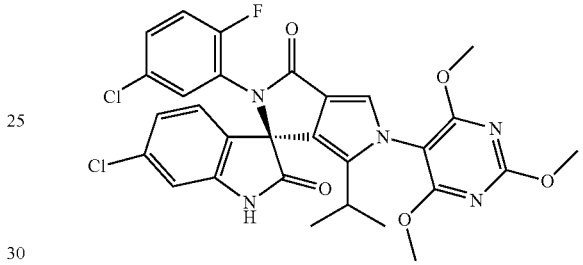

The title compound was obtained after preparative chiral SFC (method E) or chiral RP-HPLC (method L) separation of the racemic compound C-10.C5; >99% ee; t$_r$: 7.18 min. (method L'); $^1$H NMR (600 MHz, DMSO-d$_6$) δ 11.20 (s, 1H), 7.44 (ddd, J=8.9, 4.1, 2.7 Hz, 1H), 7.31 (t, J=9.1 Hz, 1H), 7.25 (s, 1H), 7.15 (dd, J=8.1, 1.7 Hz, 1H), 7.08 (dd, J=8.1, 1.9 Hz, 1H), 7.05 (dd, J=6.3, 2.7 Hz, 1H), 6.89 (d, J=1.9 Hz, 1H), 3.97 (s, 3H), 3.93 (s, 3H), 3.89 (s, 3H), 2.40-2.31 (m, 1H), 0.82 (d, J=7.1 Hz, 3H), 0.41 (d, J=7.0 Hz, 3H); $^{13}$C NMR (151 MHz, DMSO-d$_6$) δ 175.64, 167.54, 167.40, 164.33, 163.18, 158.6, 156.93, 144.05, 135.29, 133.95, 130.69, 129.61, 128.30, 127.19, 126.20, 125.74, 125.65, 123.01, 119.35, 118.69, 118.55, 111.07, 99.55, 70.08, 55.50, 55.20, 49.02, 25.42, 21.46, 21.26.

Compound C-10.C5: 6-chloro-2'-(5-chloro-2-fluorophenyl)-6'-(propan-2-yl)-5'-(trimethoxypyrimidin-5-yl)-1,2,3',5'-tetrahydro-2'H-spiro[indole-3,1'-pyrrolo[3,4-c]pyrrole]-2,3'-dione

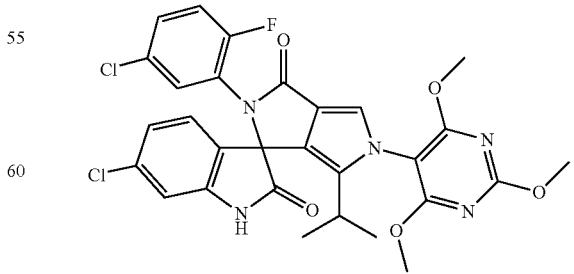

To a 100 mL flask equipped with magnetic stirring bar, compound C-9.C5 (6.7 g, 10.6 mmol) and TFA (15 mL)

were added at room temperature. The reaction mixture was stirred for 3 h at room temperature. After this time UPLCMS analysis showed 85% of the product peak area. The reaction mixture was poured on ice and extracted with DCM two times (2×30 mL). The combined organic phases were washed with water (30 mL), dried over $Na_2SO_4$ and evaporated to dryness. AcOEt (50 mL) was added to the residue and the formation of a pinkish precipitate was observed. The solid was filtered off, washed with several portions of cold AcOEt and dried on air. The desired product C-10.C5 was obtained as a pale pink solid (5.17 g, 80% yield, 99% purity according to UPLCMS analysis).

Compound C-9.C5: N-(5-chloro-2-fluorophenyl)-4-(6-chloro-3-hydroxy-2-oxo-2,3-dihydro-1H-indol-3-yl)-5-(propan-2-yl)-1-(trimethoxypyrimidin-5-yl)-1H-pyrrole-3-carboxamide

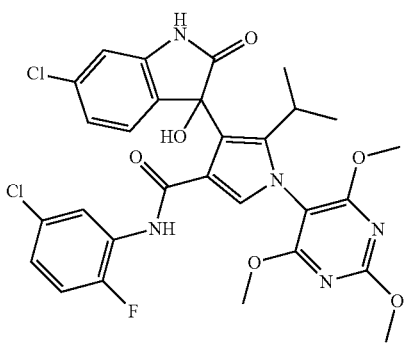 [SMILES: COc1nc(OC)c(-n2cc(C(=O)Nc3cc(Cl)ccc3F)c(C3(O)C(=O)Nc4cc(Cl)ccc43)c2C(C)C)c(OC)n1]

To a 500 mL flask equipped with magnetic stirring bar, compound C-8.C5 (5 g, 8.14 mmol, 1 eq) and THF (150 mL) were added. Then reaction mixture was cooled in an ice bath to 0° C. and trimethyl phosphite (1.92 mL, 16.3 mmol, 2 eq) was added. After 10 minutes in 0° C. sodium tert-pentoxide (3.6 g, 32.6 mmol, 4 eq) was added in several portions. The reaction mixture was stirred at room temperature (the flask was equipped with $CaCl_2$ tube) and monitored by TLC (40% AcOEt in n-hexane). Then the mixture was poured on ice and reaction was acidified with 0.5 M aqueous solution of HCl to pH ~5. After addition of DCM (100 mL) the mixture was transferred into a separatory funnel. The layers were separated and the water phase was extracted once again with DCM (100 mL). The combined organic phases were washed with brine, dried over $Na_2SO_4$ and solvent was removed in vacuo. The residue was purified by column chromatography (30%-50% AcOEt/n-hexane). The desired product C-9.C5 was obtained as a brownish solid (2.41 g, 47% yield, 96% purity according to UPLCMS analysis).

Compound C-8.C5: N-(5-chloro-2-fluorophenyl)-4-(6-chloro-2-oxo-2,3-dihydro-1H-indol-3-yl)-5-(propan-2-yl)-1-(trimethoxypyrimidin-5-yl)-1H-pyrrole-3-carboxamide

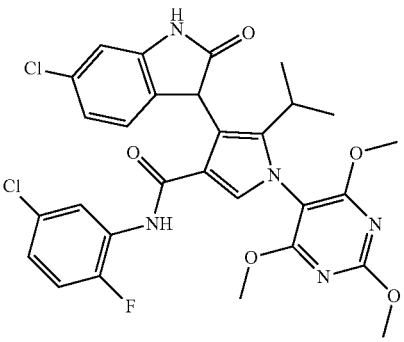 [SMILES: COc1nc(OC)c(-n2cc(C(=O)Nc3cc(Cl)ccc3F)c(C3C(=O)Nc4cc(Cl)ccc43)c2C(C)C)c(OC)n1]

In a 150 mL round-bottomed flask equipped with magnetic stirring bar, compounds C-4A (6.3 g, 25.3 mmol, 1 eq), C-6B (4.7 g, 130 mmol, 1 eq) and C-7D (5 g, 117 mmol, 1 eq) were added followed by AcOH (40 mL), and the flask was tightly closed with plastic stopper. The mixture was heated up to 80° C. and stirred at this temperature overnight. After that time UPLCMS analysis showed almost full consumption of starting materials (which equals to 66% of a product peak area). The reaction mixture was cooled to room temperature and red solid of the product C-8.C5 was filtered off, washed with AcOH and dried on air (10 g, 64% yield, 82% purity according to UPLCMS analysis).

Compound (6), C6: (3S)-6-chloro-2'-(5-chloro-2-fluorophenyl)-5'-[6-(dimethylamino)-4-methoxypyridin-3-yl]-6'-(propan-2-yl)-1,2,3',5'-tetrahydro-2'H-spiro[indole-3,1'-pyrrolo[3,4-c]pyrrole]-2,3'-dione

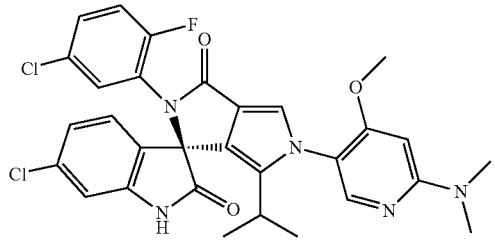 [SMILES: COc1cc(N(C)C)ncc1-n1cc2c(c1C(C)C)[C@@]1(C(=O)Nc3cc(Cl)ccc31)N(c1cc(Cl)ccc1F)C2=O]

The title compound was obtained after preparative chiral NP-HPLC (method F) or chiral RP-HPLC (method J) separation of the racemic compound C-10.C6; >99% ee; $t_r$: 14.66 min. (method J'); $^1H$ NMR (500 MHz, DMSO-$d_6$) δ 11.20 (br s, 1H), 7.91 (d, J=22.0 Hz, 1H)7.43 (ddd, J=8.9, 4.1, 2.7 Hz, 1H), 7.30 (t, J=9.1 Hz, 1H), 7.23 (s, 1H), 7.16 (dd, J=8.0, 2.1 Hz, 1H), 7.10-7.03 (m, 2H), 6.89 (d, J=1.9 Hz, 1H), 6.25 (d, J=5.6 Hz, 1H), 3.82 (d, J=20.8 Hz, 3H), 3.09 (s, 6H), 2.47-2.37 (m, 1H), 0.83 (dd, J=12.2, 7.0 Hz, 3H), 0.41 (t, J=7.0 Hz, 3H); $^{13}C$ NMR (126 MHz, DMSO-$d_6$) δ 175.77, 175.72, 164.50, 162.08, 161.95, 161.08, 158.79, 156.79, 147.23, 144.06, 135.26, 134.43, 134.39, 130.67, 130.60, 129.61, 128.30, 127.36, 127.20, 126.29, 126.23, 125.85, 125.75 123.20, 122.99, 122.94, 118.84, 11871, 118.64, 118.53, 115.45, 111.06, 88.48, 70.09, 56.06, 56.03, 38.38, 25.38, 22.01, 21.63, 21.27, 21.04.

Compound C-10.C6:6-chloro-2'-(5-chloro-2-fluorophenyl)-5'-[6-(dimethylamino)-4-methoxypyridin-3-yl]-6'-(propan-2-yl)-1,2,3',5'-tetrahydro-2'H-spiro[indole-3,1'-pyrrolo[3,4-c]pyrrole]-2,3'-dione

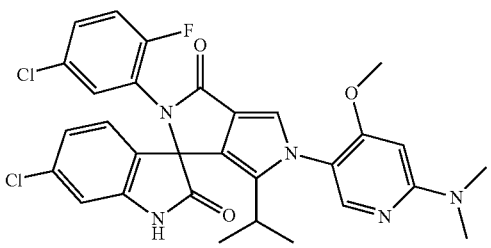 [SMILES: COc1cc(N(C)C)ncc1-n1cc2c(c1C(C)C)C1(C(=O)Nc3cc(Cl)ccc31)N(c1cc(Cl)ccc1F)C2=O]

To a 100 mL flask equipped with magnetic stirring bar, compound C-9.C6 (2.96 g, 4.8 mmol) and TFA (30 mL) were added. The reaction mixture was stirred for 1 h at 40° C. After this time UPLCMS analysis showed 97% of the desired product C-10.C6. The reaction mixture was evaporated to dryness. To the residue 20 ml of methanol and saturated NaHCO$_3$ (200 mL) were added. The suspension was refluxed for 2 h and then cooled to room temperature. The precipitate was filtered off and macerated in methanol (20 mL). The solid was collected by filtration, washed with small amount of methanol and dried in vacuo, to give the desired product C-10.C6 as the off-white solid (2.3 g, 83% yield, >99% purity according to UPLCMS analysis).

Compound C-9.C6: N-(5-chloro-2-fluorophenyl)-4-(6-chloro-3-hydroxy-2-oxo-2,3-dihydro-1H-indol-3-yl)-1-[6-(dimethylamino)-4-methoxypyridin-3-yl]-5-(propan-2-yl)-1H-pyrrole-3-carboxamide

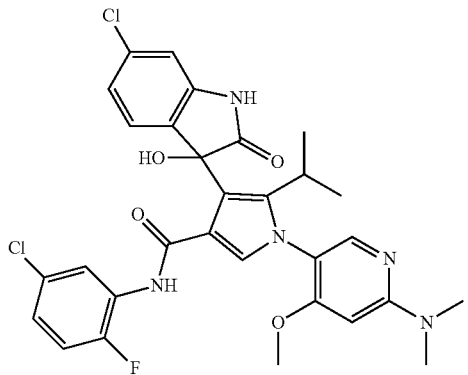 [SMILES: COc1cc(N(C)C)ncc1-n1cc(C(=O)Nc2cc(Cl)ccc2F)c(C2(O)C(=O)Nc3cc(Cl)ccc32)c1C(C)C]

To a 100 mL flask equipped with magnetic stirring bar, compound C-8.C6 (4 g, 6.7 mmol, 1 eq) and THF (30 mL) were added followed by triethyl phosphite (1.72 mL, 10.1 mmol, 1.5 eq). Then, the mixture was cooled to 3° C. and sodium tert-pentoxide (1.48 g, 13.4 mmol, 2 eq) was added in several portions. After heating up to room temperature the reaction mixture was stirred for 22 h (the flask was equipped with CaCl$_2$ tube). After that time UPLCMS analysis showed 94% of the desired product C-9.C6. To the mixture was added water (200 mL) and 1 M HCl to reach pH ~8. The aqueous phase was extracted with AcOEt (3×150 mL). The organic phases were combined and dried over MgSO$_4$. After concentration, the crude material was further purified by chromatography (10-30% i-PrOH/n-hexane) to afford compound C-9.C6 (3 g, 72% yield, 94% purity according to UPLCMS analysis).

Compound C-8.C6: N-(5-chloro-2-fluorophenyl)-4-(6-chloro-2-oxo-2,3-dihydro-1H-indol-3-yl)-1-[6-(dimethylamino)-4-methoxypyridin-3-yl]-5-(propan-2-yl)-1H-pyrrole-3-carboxamide

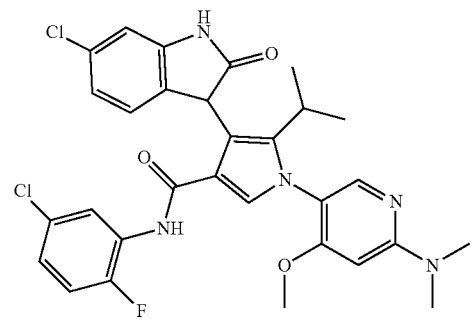 [SMILES: COc1cc(N(C)C)ncc1-n1cc(C(=O)Nc2cc(Cl)ccc2F)c(C2C(=O)Nc3cc(Cl)ccc32)c1C(C)C]

In a round-bottom pressure flask (250 mL) equipped with magnetic stirring bar, compounds C-4A (5.37 g, 21.5 mmol, 1 eq), C-7C (3.6 g, 21.5 mmol, 1 eq), C-6B (4.25 g, 21.5 mmol, 1 eq) and PTSA.H$_2$O (4.09 g, 21.5 mmol, 1 eq) were suspended in water (9 mL) and methanol (36 mL). The flask was tightly closed and then mixture was heated up to 60° C. and stirred at this temperature for 23 h. After that time UPLCMS analysis showed 17% of the expected product C-8.C6. Then, additional portion of compound C-6B (1.06 g, 5.4 mmol) was added, and the mixture was heated up to 75° C. and stirred at this temperature for 42 h. The sample was taken and UPLCMS analysis showed 58% of the expected product C-8.C6. The reaction mixture was evaporated to dryness. To the residue were added DCM (200 mL), 5% solution of NaHCO$_3$ (150 mL) and the mixture was stirred for 20 min. The aqueous phase was extracted with DCM (4×200 mL). Organic phases were combined and dried over MgSO$_4$. After concentration, the crude material was purified by column chromatography (20-50% AcOEt/n-hexane) to afford compound C-8.C6 (4.1 g, 32% yield, 90% purity according to UPLCMS analysis).

Compound (7), C7: (3S)-6-chloro-2'-(3,4-difluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

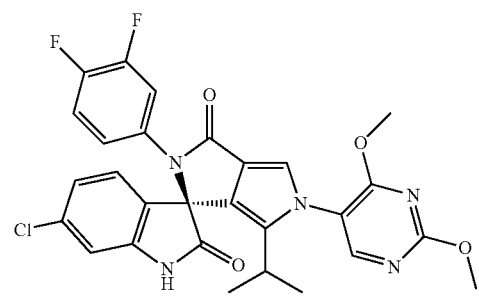 [SMILES: COc1ncc(-n2cc3c(c2C(C)C)[C@@]2(C(=O)Nc4cc(Cl)ccc42)N(c2ccc(F)c(F)c2)C3=O)c(OC)n1]

The title compound was obtained after preparative chiral SFC (method G) or chiral RP-HPLC (method O) separation of the racemic compound C-10.C7; >99% ee; t$_r$: 5.61 min (method O'). $^1$H NMR (500 MHz, CDCl$_3$) δ 6.76 (br s, 1H), 8.23 (s, 1H), 7.23-7.18 (m, 1H), 7.11-7.06 (m, 1H), 7.06-6.98 (m, 2H), 6.98-6.90 (m, 1H), 6.90-6.85 (m, 1H), 6.83-6.76 (m, 1H), 4.06 (s, 3H), 3.99 (s, 3H), 2.49-2.39 (m, 1H), 0.90 (d, J=7.0 Hz, 3H), 0.51 (d, J=7.0 Hz, 3H); $^{13}$C NMR (125 MHz, CDCl$_3$) δ 175.3, 166.5, 165.7, 164.9, 157.0, 150.9, 149.0, 148.9, 148.8, 142.2, 136.4, 134.3, 132.3, 126.5, 126.2, 124.9, 123.7, 122.9, 120.6, 118.1, 118.0, 117.8, 117.5, 117.4, 116.1, 111.7, 77.3, 77.0, 76.7, 70.2, 55.6, 54.7, 25.6, 21.3.

Compound C-10.C7: 6-chloro-2'-(3,4-difluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

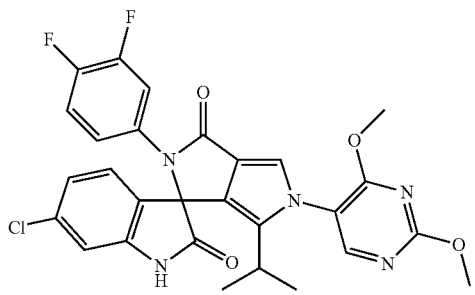 [SMILES: COc1ncc(-n2cc3c(c2C(C)C)C2(C(=O)Nc4cc(Cl)ccc42)N(c2ccc(F)c(F)c2)C3=O)c(OC)n1]

To a 250 mL flask equipped with magnetic stirring bar, compound C-9.C7 (7.34 g, 15.57 mmol) and TFA (80 mL) were added at room temperature (TFA was added around 5 mL/min). Then, the reaction was stirred for 3 h at 40° C. After this time UPLCMS analysis showed 84% of of product peak area. The mixture was cooled to room temperature and evaporated to dryness. Crude product was purified by flash column chromatography (20%-50% AcOEt/n-hexane). After removing of solvents product C-10.C7 was obtained as a light brown solid/foam (4.45 g, 63% yield after two steps synthesis) with 93% of purity according to UPLCMS analysis.

Compound C-9.C7: 4-(6-chloro-3-hydroxy-2-oxo-2,3-dihydro-1H-indol-3-yl)-N-(3,4-difluorophenyl)-1-(2,4-dimethoxypyrimidin-5-yl)-5-(propan-2-yl)-1H-pyrrole-3-carboxamide

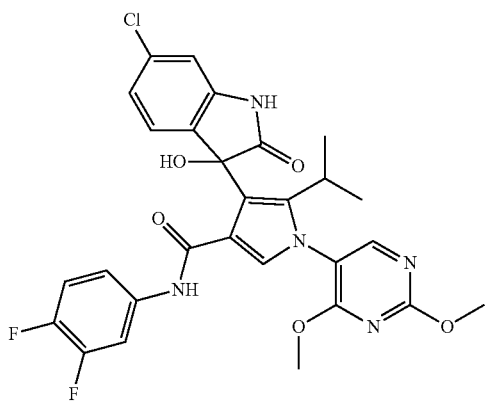 [SMILES: COc1ncc(-n2cc(C(=O)Nc3ccc(F)c(F)c3)c(C3(O)C(=O)Nc4cc(Cl)ccc43)c2C(C)C)c(OC)n1]

To a 500 mL flask equipped with magnetic stirring bar, compound C-8.C7 (7.14 g, 12.57 mmol, 1 eq) and THF (140 mL) were added. Then, the reaction mixture was cooled in an ice bath to 0° C. and trimethyl phosphite (2.25 mL, 18.86 mmol, 1.5 eq), followed by sodium tert-pentoxide (2.77 g, 25.14 mmol, 2 eq) were added in one portion. The reaction mixture was stirred for 1.5 h at 0° C. (the flask was equipped with CaCl$_2$ tube). After this time UPLCMS analysis showed 88% of product peak area Cold water (50 mL) was added and the reaction was acidified with 5% HCl to pH ~5. The reaction mixture was stirred for around 0.5 h at room temperature and the resulting precipitate was filtered off and washed with 100 mL of cold water. Thus obtained solid was redissolved in AcOEt, washed with water, dried over Na$_2$SO$_4$ and the solvent was evaporated. The crude product C-9.C7 was obtained as brown solid (83% purity according to UPLCMS analysis) and was used in the next step without any further purification.

Compound C-8.C7: 4-(6-chloro-2-oxo-2,3-dihydro-1H-indol-3-yl)-N-(3,4-difluorophenyl)-1-(2,4-dimethoxypyrimidin-5-yl)-5-(propan-2-yl)-1H-pyrrole-3-carboxamide

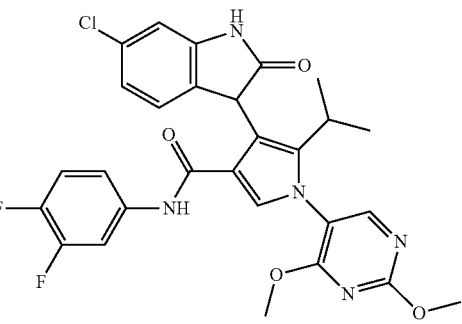

To a 250 mL sealed tube equipped with magnetic stirring bar, compounds C-4A (12.48 g, 50 mmol, 1 eq), C-7A (7.76 g, 50 mmol, 1 eq) and C-6E (9.06 g, 50 mmol, eq) were added followed by AcOH (100 mL), and the tube was tightly closed with plastic stopper. The mixture was heated up to 80° C. (temperature of the heating bath) and stirred at this temperature overnight. After that time UPLCMS analysis showed almost full consumption of starting materials (which equals to 40% of a product peak area). The reaction mixture was cooled to room temperature and AcOH was evaporated to dryness. The residue was preadsorbed onto silicagel and purified by chromatography (50% of AcOEt/n-hexane). After removing of solvents product C-8.C7 was obtained as a dark brown solid/foam (7.63 g, 24.9% yield, 84% of purity according to UPLCMS analysis.

Compound (8), C8: (3S)-6-chloro-2'-(3,4-difluorophenyl)-5'-(4,6-dimethoxypyridin-3-yl)-6'-(propan-2-yl)-1,2,3',5'-tetrahydro-2'H-spiro[indole-3,1'-pyrrolo[3,4-c]pyrrole]-2,3'-dione

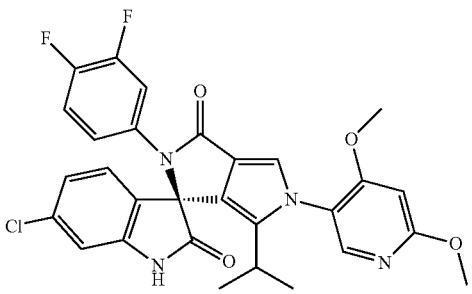 [SMILES: COc1cc(OC)c(-n2cc3c(c2C(C)C)[C@@]2(C(=O)Nc4cc(Cl)ccc42)N(c2ccc(F)c(F)c2)C3=O)cn1]

The title compound was obtained after preparative chiral SEC (method H) or chiral RP-HPLC (method N) separation of the racemic compound C-10.C8; >99% ee; t$_r$: 6.2 min. (method N'); $^1$H NMR (500 MHz, DMSO-d$_6$) δ 11.15 (br s, 1H), 8.07 (d, J=34.9 Hz, 1H). 7.46-7.37 (m, 1H), 7.37-7.27 (m, 2H), 7.15 (m, 1H), 7.08 (dd, J=8.0, 1.9 Hz, 1H), 6.92 (m, J=2.2 Hz, 1H), 6.85 (m, 1H), 6.64 (d, J=4.0 Hz, 1H), 3.90 (s, 3H), 3.83 (d, J=23.6 Hz, 3H), 2.37 (m, 1H), 0.85 (dd, J=13.0, 7.0 Hz, 3H), 0.41 (dd, J=9.4, 6.9 Hz, 3H); $^{13}$C NMR (125 MHz, DMSO-d$_6$) δ 175.18, 175.05, 165.31, 164.56, 162.80, 162.74, 149.75, 149.64, 147.79, 147.68, 147.33, 147.24, 145.92, 145.79, 143.48, 143.43, 134.62, 134.59, 133.42, 127.08, 126.18, 126.10, 122.71, 122.67, 122.58, 120.23, 119.41, 117.79, 117.70, 117.55, 117.23, 117.09, 110.62, 93.37, 93.29, 69.61, 56.21, 53.64, 24.90, 21.39, 21.08, 20.64, 20.50.

Compound C-10.C8: 6-chloro-2'-(3,4-difluorophenyl)-5'-(4,6-dimethoxypyridin-3-yl)-6'-(propan-2-yl)-1,2,3',5'-tetrahydro-2'H-spiro[indole-3,1'-pyrrolo[3,4-c]pyrrole]-2,3'-dione

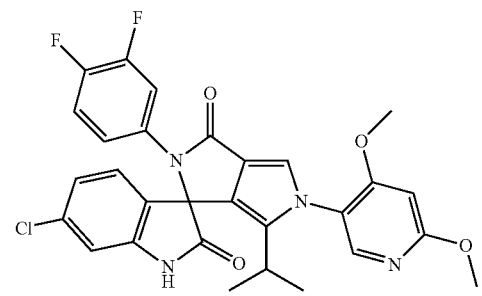 [SMILES: COc1cc(OC)c(-n2cc3c(c2C(C)C)C2(C(=O)Nc4cc(Cl)ccc42)N(c2ccc(F)c(F)c2)C3=O)cn1]

To a 100 mL flask equipped with magnetic stirring bar, compound C-9.C8 (2 g, 3.5 mmol) was added and flask was cooled in an ice bath. Then, TEA (20 mL) was added slowly (around 2 mL/min). Cooling bath was removed and reaction was stirred 1 h at room temperature. After this time UPLCMS analysis showed 75% of product peak. The reaction was stirred additional 1 h and the mixture was poured into ice (around 50 g) and diluted with DCM (50 mL). Phases were separated and the water phase was extracted with DCM three times (3×50 mL). The combined organic phases were washed with water, brine and solvent was removed in vacuo. The residue was preadsorbed onto silicagel and purified using flash chromatography (50% of AcOEt in n-hexane). After removing of solvents product C-10.C8 was obtained as the red-brown solid/foam (815 mg, 41% yield) with 98% of purity, according to UPLCMS analysis. Above reaction was repeated three more times and all obtained samples (5.76 g) of compound C-10.C8 were combined and stirred in the 25 mL mixture of AcOEt/n-hexane (1:5). The mixture was heated to reflux and AcOEt was added until all remaining solid was dissolved. Then 75 mL of n-hexane was added dropwise and the mixture was stirred 16 h at room temperature. The solid was filtered, washed with AcOEt/n-hexane (1:10, 25 mL) and dried under high vacuum. As a result, the final product C-1.C8 was obtained as a light red solid (4.77 g, 98% of purity, according to UPLCMS analysis).

Compound C-9.C8: 4-(6-chloro-3-hydroxy-2-oxo-2,3-dihydro-1H-indol-3-yl)-N-(3,4-difluorophenyl)-1-(4,6-dimethoxypyridin-3-yl)-5-(propan-2-yl)-1H-pyrrole-3-carboxamide

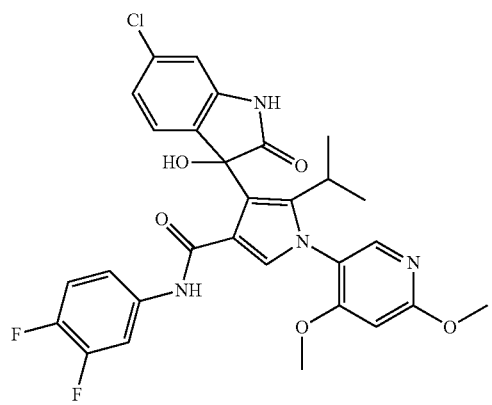 [SMILES: COc1cc(OC)c(-n2cc(C(=O)Nc3ccc(F)c(F)c3)c(C3(O)C(=O)Nc4cc(Cl)ccc43)c2C(C)C)cn1]

To a 100 mL flask equipped with magnetic stirring bar, compound C-8.C8 (2 g, 3.5 mmol, 1 eq) and THF (35 mL) were added followed by trimethyl phosphite (0.83 mL, 7 mmol, 2 eq). Then, reaction mixture was cooled in an ice bath and sodium tert-pentoxide (1.54 g, 14 mmol, 4 eq) was added in one portion. Cooling bath was removed and reaction was stirred 1 h at room temperature (the flask was equipped with CaCl$_2$ tube). After that time UPLCMS analysis showed 80% of the product peak area. After one more hour of stirring, around 90% of the solvent was removed and such obtained mixture was diluted with 50 g of ice. Obtained suspension was acidified with 1 M HCl to pH ~5 and additionally diluted with 50 mL of DCM. The phases were separated and the aqueous phase was extracted with DCM (2×30 mL). The combined organic phases were washed with water, brine, dried over Na$_2$SO$_4$ and solvent was removed in vacuo. The crude product C-9.C8 was obtained as a red-black solid/foam (70% purity according to UPLCMS analysis) and was used in the next step without any further purification (yield was exceeded 100%).

Compound C-8.C8: 4-(6-chloro-2-oxo-2,3-dihydro-1H-indol-3-yl)-N-(3,4-difluorophenyl)-1-(4,6-dimethoxypyridin-3-yl)-5-(propan-2-yl)-1H-pyrrole-3-carboxamide

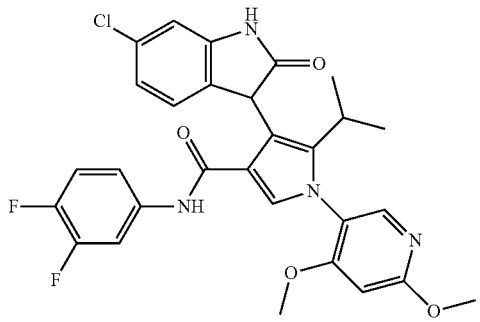 [SMILES: COc1cc(OC)c(-n2cc(C(=O)Nc3ccc(F)c(F)c3)c(C3C(=O)Nc4cc(Cl)ccc43)c2C(C)C)cn1]

To a 500 mL flask equipped with magnetic stirring bar, compounds C-4A (8.1 g, 32.4 mmol, 1 eq), C-7B (5 g, 32.4 mmol, 1 eq) and C-6E (5.9 g, 32.4 mmol, 1 eq) were added followed by AcOH (80 mL), and the flask was tightly closed with plastic stopper. The mixture was heated up to 85° C. (temperature of the heating bath) and stirred at this temperature for 16 h. After this time UPLCMS analysis showed almost full consumption of starting materials (which equals to 55% of a product peak area). Reaction mixture was cooled to room temperature and AcOH was evaporated to dryness. The residue was preadsorbed onto silicagel and purified using flash chromatography (30% to 60% of AcOEt in n-hexane). After removing of solvents product C-8.C8 was obtained as a light red solid (8 g, 44% yield) with 87% of purity according to UPLCMS analysis.

Compound (9), C9: (3S)-6-chloro-2'-(5-chloro-2-fluorophenyl)-5'-(4,6-dimethoxypyridin-3-yl)-6'-(propan-2-yl)-1,2,3',5'-tetrahydro-2'H-spiro[indole-3,1'-pyrrolo[3,4-c]pyrrole]-2,3'-dione

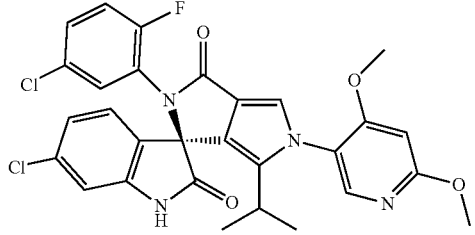 [SMILES: COc1cc(OC)c(-n2cc3c(c2C(C)C)[C@@]2(C(=O)Nc4cc(Cl)ccc42)N(c2cc(Cl)ccc2F)C3=O)cn1]

The title compound was obtained after preparative chiral SFC (method I) or chiral RP-HPLC (method S) separation of the racemic compound C-10.C9; >99% ee; $t_r$: 8.85 min (method S'). $^1$H NMR (500 MHz, DMSO-$d_6$) δ 11.23 (br s, 1H), 8.10 (d, J=26.0 Hz, 1H), 7.44 (ddd, J=8.9, 4.1, 2.7 Hz, 1H), 7.35-7.27 (m, 2H), 7.17 (dd, J=8.1, 1.8 Hz, 1H), 7.10-7.02 (m, 2H), 6.90 (d, J=1.9 Hz, 1H), 6.64 (d, J=2.1 Hz, 1H), 3.90 (s, 3H), 3.83 (d, J=20.7 Hz, 3H), 2.45-2.32 (m, 1H), 0.84 (dd, J=9.4, 7.0 Hz, 3H), 0.42 (dd, J=7.1, 4.0 Hz, 3H); $^{13}$C NMR (126 MHz, DMSO-$d_6$) δ 175.68, 165.85, 164.38, 163.36, 163.24, 158.77, 156.77, 146.44, 144.17, 135.31, 134.21, 130.70, 129.60, 128.33, 127.33, 126.18, 125.78, 125.66, 123.46, 122.92, 120.71, 119.27, 118.72, 118.54, 111.11, 93.90, 70.08, 56.78, 54.18, 25.42, 22.00, 21.64, 21.24, 21.04.

Compound C-10.C9: 6-chloro-2'-(5-chloro-2-fluorophenyl)-5'-(4,6-dimethoxypyridin-3-yl)-6'-(propan-2-yl)-1,2,3',5'-tetrahydro-2'H-spiro[indole-3,1'-pyrrolo[3,4-c]pyrrole]-2,3'-dione

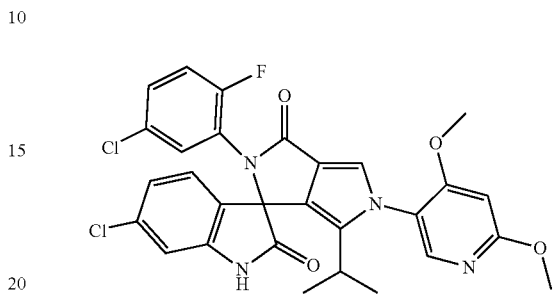

In a 100 mL flask equipped with magnetic stirring bar, compound C-9.C9 (5.8 g, 9.68 mmol) was dissolved in 30 mL of anhydrous DCM and 10 mL of TFA was added in one portion. Reaction was stirred 3 h at room temperature. After this time UPLCMS analysis showed 54% of product peak area. Reaction mixture was evaporated to dryness. Residue was stirred in 30 mL of AcOEt for 1 h and pale-gray solid precipitated from the mixture. The solid was separated by filtration and dried on air. As a result, product C-10.C9 was obtained (2.2 g, 34.1% yield after 2 steps, starting from C-8.C9, 94% purity according to UPLCMS analysis).

Compound C-9.C9: N-(5-chloro-2-fluorophenyl)-4-(6-chloro-3-hydroxy-2-oxo-2,3-dihydro-1H-indol-3-yl)-1-(4,6-dimethoxypyridin-3-yl)-5-(propan-2-yl)-1H-pyrrole-3-carboxamide

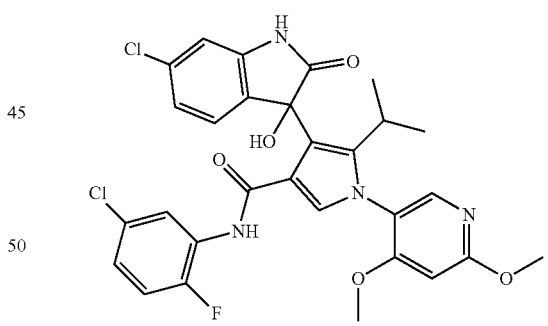

To a 100 mL flask equipped with magnetic stirring bar, compound C-8.C9 (6.08 g, 10.5 mmol, 1 eq) and THF (62 mL) were added followed by trimethyl phosphite (2.47 ml, 21 mmol, 2 eq). Then, reaction mixture was cooled in an ice bath and sodium tert-pentoxide (3.47 g, 31.5 mmol, 3 eq) was added in one portion. Cooling bath was removed and reaction was stirred 1 h at room temperature (the flask was equipped with CaCl$_2$ tube). After this time UPLCMS analysis showed 94% of the product peak area. Reaction mixture was cooled to around −10° C. then it was poured on ice and reaction was acidified with 0.5 M HCl to pH ~5. The aqueous phase was extracted with AcOEt (3×100 mL), dried over Na$_2$SO$_4$ and the solvent was evaporated in vacuo. The crude product C-9.C9 was obtained as a red-black solid/foam (68% purity according to UPLCMS analysis) and was used in the next step without any further purification (yield was exceeded 100%).

Compound C-8.C9: N-(5-chloro-2-fluorophenyl)-4-(6-chloro-2-oxo-2,3-dihydro-1H-indol-3-yl)-1-(4,6-dimethoxypyridin-3-yl)-5-(propan-2-yl)-1H-pyrrole-3-carboxamide

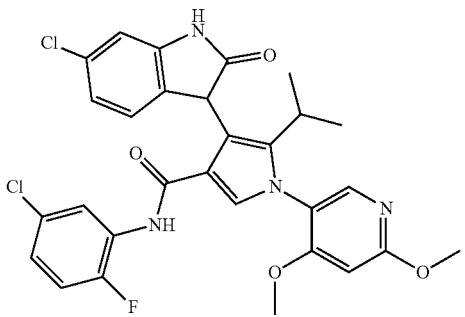 [SMILES: COc1cc(OC)c(-n2cc(C(=O)Nc3cc(Cl)ccc3F)c(C3C(=O)Nc4cc(Cl)ccc43)c2C(C)C)cn1]

To a 100 mL flask equipped with magnetic stirring bar, compounds C-4A (7.79 g, 30 mmol, 1 eq), C-7B (4.68 g, 30 mmol, 1 eq) and C-6B (6 g, 30 mmol, 1 eq) were added followed by AcOH (60 mL), and the flask was tightly closed with plastic stopper. The mixture was heated up to 85° C. (temperature of the heating bath) and stirred at this temperature for 16 h. After that time UPLCMS analysis showed almost full consumption of starting materials (which equals to 40% of a product peak area). Reaction mixture was cooled to around 15° C. and abundant red solid precipitate was separated by filtration from the reaction mixture. The filtrate was evaporated to dryness. The residue was preadsorbed onto silicagel and purified using flash chromatography (10% to 60% of AcOEt in n-hexane). After removing of the solvents product C-8.C9 was obtained as a light red solid (5.58 g, 31.5% yield) with 93% of purity according to UPLCMS analysis.

Compound (10), C10: (3S)-6-chloro-2'-(5-chloro-2,4-difluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

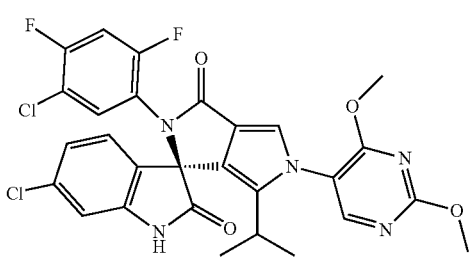 [SMILES: COc1ncc(-n2cc3c(c2C(C)C)[C@@]2(C(=O)Nc4cc(Cl)ccc42)N(c2cc(Cl)c(F)cc2F)C3=O)c(OC)n1]

The title compound was obtained after preparative chiral RP-HPLC separation of the racemic compound C-10.C10 using the method P; >99% ee; $t_r$: 9.96 min. (method P'); $^1$H NMR (500 MHz, DMSO-d$_6$) δ 11.22 (br s, 1H). 8.50 (br s, 1H), 7.64 (t, J=9.4 Hz, 1H), 7.40 (s, 1H), 7.20 (t, J=7.5 Hz, 2H), 7.10 (dd, J=8.0, 2.0 Hz, 1H), 6.91 (d, J=1.9 Hz, 1H), 3.98 (s, 3H), 3.95 (s, 3H), 2.47-2.41 (m, 1H), 0.85 (d, J=7.0 Hz, 3H), 0.44 (d, J=6.9 Hz, 3H); $^{13}$C NMR (126 MHz, DMSO-d$_6$) δ 175.36, 170.76, 166.43, 164.71, 164.35, 159.05, 158.96, 158.36, 158.26, 157.95, 157.03, 156.93, 156.36, 156.26, 144.01, 135.46, 134.20, 131.13, 127.41, 125.84, 123.55, 123.09, 121.72, 121.63, 119.46, 118.77, 116.23, 115.59, 115.44, 111.19, 107.31, 107.10, 106.90, 70.05, 60.19, 55.66, 55.01, 25.34, 22.31-20.83

Compound C-10.C10: 6-chloro-2'-(5-chloro-2,4-difluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione

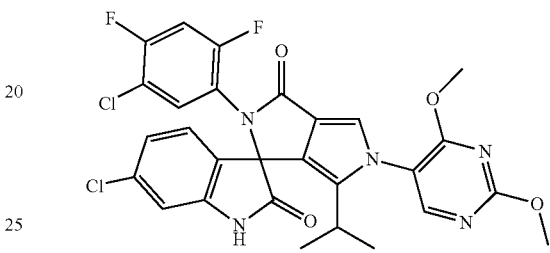

AcOH (25 mL) was placed in a 100 mL flask equipped with magnetic stirring bar. Then, C-9.C10 (2.3 g, 4 mmol, 1 eq) was added in one portion. MsOH (0.25 mL, 4.85 mmol, 1.2 eq) added dropwise and the mixture was stirred for 2 h at 45° C. Most of the AcOH was evaporated and the residue was dissolved in DCM (100 mL), then 100 mL water was added, and the mixture was treated with 3 M NaOH to reach pH ~8. Phases were separated and the water phase was extracted with DCM (2×100 mL). The combined organic phases were washed with brine (50 mL), dried over MgSO$_4$ and concentrated. The residue was purified by flash chromatography (CHCl$_3$:MeOH; 100:0→98:2) obtaining 1.7 g of the product C-10.C10 with 91% purity according to UPLCMS analysis.

Compound C-9.C10: N-(5-chloro-2,4-difluorophenyl)-4-(6-chloro-3-hydroxy-2-oxo-2,3-dihydro-1H-indol-3-yl)-1-(2,4-dimethoxypyrimidin-5-yl)-5-(propan-2-yl)-1H-pyrrole-3-carboxamide

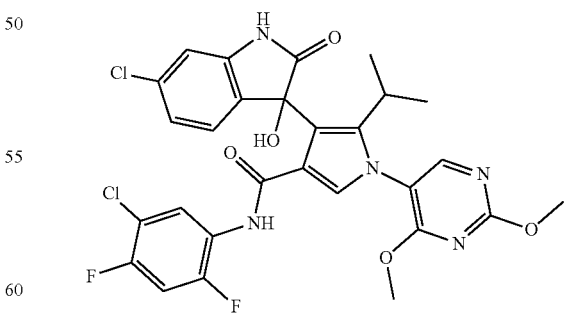

To a 100 mL flask equipped with magnetic stirring bar, compound C-8.C10 (8.9 g, 14.8 mmol, 1 eq) and THF (50 mL) were added followed by triethyl phosphite (3.8 mL, 22.2 mmol, 1.5 eq). The solution was cooled to 0° C. and then sodium tert-butoxide (2.85 g, 29.6 mmol, 2 eq) was added in several portions. The reaction mixture was stirred for 3 h at room temperature (the flask was equipped with CaCl$_2$) tube). After that time UPLCMS analysis showed 82% of the desired product. The reaction mixture was slowly poured into a chilled (0-5° C.) mixture of water (150 mL) and 36% HCl (5 mL). After addition of ethyl acetate (100 mL) the mixture was transferred into a separatory funnel. The layers were separated and the water phase was extracted once again with AcOEt (100 mL). The combined organic phases were washed with brine, dried over MgSO$_4$ and concentrated in vacuo. The oily residue was preadsorbed onto silicagel and purified using flash chromatography (DCM/MeOH 100:0→98:2). Two fractions of the product C-9.C10 were isolated: 3 g with 85% purity, and 3 g with 41% purity according to UPLCMS analysis. Yield: 50% (including both fractions).

Compound C-8.C10; N-(5-chloro-2,4-difluorophenyl)-4-(6-chloro-2-oxo-2,3-dihydro-1H-indol-3-yl)-1-(2,4-dimethoxypyrimidin-5-yl)-5-(propan-2-yl)-1H-pyrrole-3-carboxamide

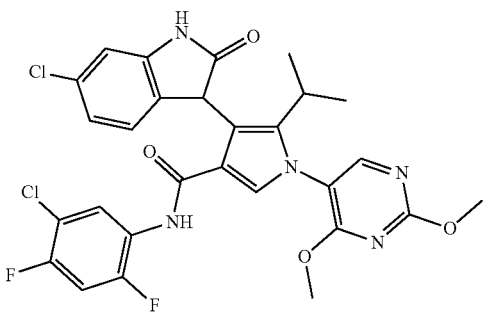 [SMILES: COc1ncc(-n2cc(C(=O)Nc3cc(Cl)c(F)cc3F)c(C3C(=O)Nc4cc(Cl)ccc43)c2C(C)C)c(OC)n1]

In a 250 mL round-bottomed flask equipped with magnetic stirring bar, compounds C-4A (11.6 g, 47 mmol, 1 eq), C-7A (8.7 g, 56 mmol, 1.2 eq) and C-6F (10 g, 47 mmol, 1 eq) were suspended in 75 mL of AcOH, and the flask was tightly closed with plastic stopper. The mixture was heated up to 70° C. and stirred at this temperature for 24 h. After that time UPLCMS analysis showed 47% of the expected product. The reaction mixture was evaporated to dryness. The solid residue was preadsorbed onto silicagel and purified using flash chromatography (20% to 50% of AcOEt in n-hexane). All fractions which contained the product were evaporated to dryness to furnish 6.6 g of the desired product C-8.C10, with 83% purity according to UPLCMS analysis. Yield: 32%.

Compound (11), C11: (3)-6'-(butan-2-yl)-6-chloro-2'-(5-chloro-2-fluorophenyl)-5'-(2,4-dimethoxypyrimidin-5-yl)-1,2,3',5'-tetrahydro-2'H-spiro[indole-3,1'-pyrrolo[3,4-c]pyrrole]-2,3'-dione

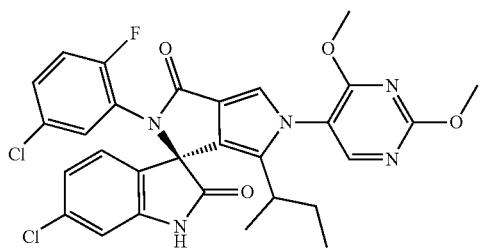 [SMILES: CCC(C)c1c2c(cn1-c1cnc(OC)nc1OC)C(=O)N(c1cc(Cl)ccc1F)[C@]21C(=O)Nc2cc(Cl)ccc21]

The title compound (diastereomeric mixture) was obtained after preparative chiral HPLC-RP separation of the racemic compound C-10.C11 using the method M; >99% ee; t$_r$: 9.96 min. (method M'); $^1$H NMR (500 MHz, DMSO-d$_6$) δ 11.24 (s, 1H), 8.50 (br s, 1H), 7.44 (ddd, J=8.9, 4.2, 2.7 Hz, 1H), 7.38 (s, 1H), 7.31 (t, J=9.1 Hz, 1H), 7.23-7.14 (m, 1H), 7.03 (dd, J=6.4, 2.7 Hz, 1H), 6.84 (ddd, J=10.5, 8.4, 2.4 Hz, 1H), 6.72 (dd, J=8.9, 2.4 Hz, 1H), 3.98 (s, 3H), 3.95 (br s, 3H), 3.09 (q, J=7.3 Hz, 2H), 2.48-2.39 (m, 1H), 1.18 (t, J=7.2 Hz, 3H), 0.85 (d, J=7.0 Hz, 2H), 0.44 (d, J=7.0 Hz, 3H); $^{13}$C NMR (126 MHz, DMSO-d$_6$) δ 175.83, 166.45, 164.83, 164.70, 164.26, 162.87, 158.76, 157.95, 156.76, 144.36, 144.26, 134.08, 130.72, 130.66, 129.55, 128.30, 128.28, 127.61, 127.53, 125.73, 125.61, 123.86, 122.88, 119.71, 118.70, 118.59, 118.52, 116.26, 109.68, 109.50, 99.43, 99.21, 70.02, 55.66, 55.01, 46.14, 25.33, 21.51, 11.45, 9.08.

Compound C-10.C11: 6'-(butan-2-yl)-6-chloro-2'-(5-chloro-2-fluorophenyl)-5'-(2,4-dimethoxypyrimidin-5-yl)-1,2,3',5'-tetrahydro-2'H-spiro[indole-3,1'-pyrrolo[3,4-c]pyrrole]-2,3'-dione

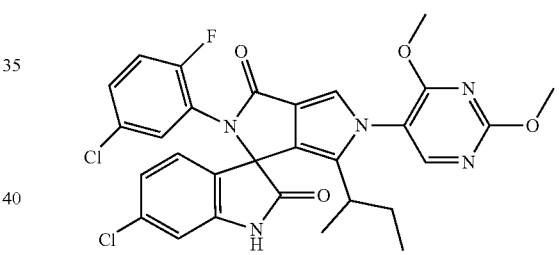

To a 250 mL flask equipped with magnetic stirring bar, compound C-9.C11 (2.8 g, 4.56 mmol) was added along with DCM (60 mL). Then, TFA (30 mL) was added (around 2 mL/min). Reaction was stirred for 2 h at room temperature. After that time UPLCMS analysis showed 65% of expected product peak area. The mixture was then poured on ice (around 200 mL) and diluted with DCM (100 mL). The phases were separated and the water phase was extracted with DCM three times (3×50 mL). The combined organic phases were washed with water, brine, dried over MgSO$_4$ and concentrated under vacuum. The crude product C-10.C11 was purified using column chromatography (10% to 40% of acetone in n-hexane). As a result, 1.5 g of brown solid C-10.C11 was obtained. This solid was stirred in AcOEt (5 mL), separated by filtration, washed with 20 mL of AcOEt and dried on air. As a result, product C-10.C11 was obtained as a white participate (1.4 g, 98% of purity according to UPLCMS analysis).

Compound C-9.C11: 5-(butan-2-yl)-N-(5-chloro-2-fluorophenyl)-4-(6-chloro-3-hydroxy-2-oxo-2,3-dihydro-1H-indol-3-yl)-1-(2,4-dimethoxypyrimidin-5-yl)-1H-pyrrole-3-carboxamide

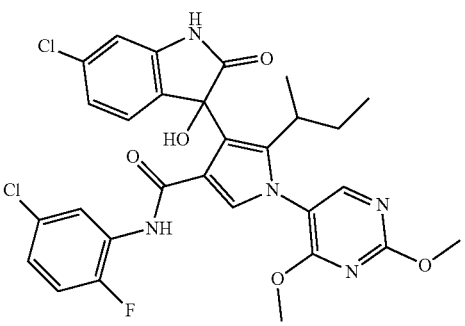 [SMILES: CCC(C)c1c(C2(O)C(=O)Nc3cc(Cl)ccc32)c(C(=O)Nc2cc(Cl)ccc2F)cn1-c1cnc(OC)nc1OC]

To a 250 mL flask equipped with magnetic stirring bar, compound C-8.C11 (3 g, 5 mmol, 1 eq) and THF (80 mL) were added followed by trimethyl phosphite (1.21 mL, mmol, 2 eq). Then, reaction mixture was cooled in an ice bath and sodium tert-pentoxide (2.2 g, 20 mmol, 4 eq) was added in small portions. The cooling bath was removed and reaction was stirred for 5 h at room temperature (the flask was equipped with $CaCl_2$) tube). After that time UPLCMS analysis showed 71% of two (diastereomeric) peaks of the product C-9.C11. Reaction mixture was diluted with 200 mL of water with ice. The obtained suspension was acidified with 3 M HCl to pH ~5 and diluted with 100 mL of AcOEt. The phases were separated and the water phase was extracted with AcOEt three times (3×50 mL). The combined organic phases were washed with water, brine, dried over $Na_2SO_4$ and solvent was removed in vacuo. The crude product C-9.C11 was obtained as a dark red oil (72% purity according to UPLCMS analysis) and was used in the next step without any further purification.

Compound C-8.C11: 5-(butan-2-yl)-N-(5-chloro-2-fluorophenyl)-4-(6-chloro-2-oxo-2,3-dihydro-1H-indol-3-yl)-1-(2,4-dimethoxypyrimidin-5-yl)-1H-pyrrole-3-carboxamide

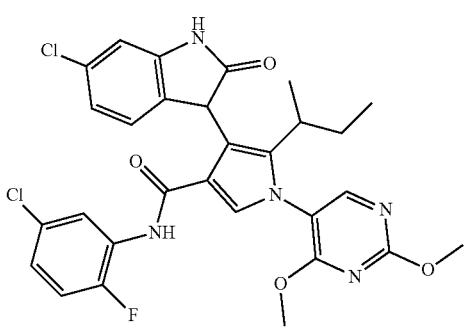 [SMILES: CCC(C)c1c(C2C(=O)Nc3cc(Cl)ccc32)c(C(=O)Nc2cc(Cl)ccc2F)cn1-c1cnc(OC)nc1OC]

To a 250 mL flask equipped with magnetic stirring bar, compounds C-4B (4.44 g, 16.8 mmol, 1 eq), C-7A (2.87 g, 18.5 mmol, 1.1 eq) and C-6F (3.32 g. 16.8 mmol, 1 eq) were added followed by AcOH (30 mL), and the flask was tightly closed with plastic stopper. The mixture was heated up to 90° C. (temperature of the heating bath) and stirred at this temperature for 16 h. After that time UPLCMS analysis showed almost full consumption of starting materials (which equals to 50% of a product peak area). The reaction mixture was cooled to room temperature and evaporated to dryness. The residue was preadsorbed onto silicagel and purified using flash chromatography (30% to 60% of AcOEt in n-hexane). After removing of solvents product C-8.C11 was obtained as a dark red solid/foam (3.5 g, 35% yield) with 83% of purity according to UPLCMS analysis.

Obtaining and Analysis of Enantiomers

All enantiomers were separated on preparative SFC or HPLC with chiral columns.

Chiral Purification Conditions—SFC

Method A: column: Lux Amylose-1 (21.2 mm×250 mm, 5 μm), flow 50 mL/min, isocratic elution $MeOH:CO_2$, 25:75, detection: UV 210 nm Method B: column: Lux Cellulose-1 (21.2 mm×250 mm, 5 μm), flow 50 mL/min, isocratic elution $MeOH:CO_2$, 25:75, detection: UV 210 nm Method C: column: Lux Cellulose-4 (21.2 mm×250 mm, 5 μm), flow 50 mL/min, isocratic elution $MeOH:CO_2$, 45:55, detection: UV 215 nm Method D: column: Chiralpak IC (20 mm×250 mm, 5 μm), flow 21 mL/min, isocratic elution $EtOH:CO_2$, 45:55, detection: UV 210 nm Method E: column: Lux Cellulose-4 (21.2 mm×250 mm, 5 μm), flow 50 mL/min, isocratic elution $MeOH:CO_2$, 40:60, detection: UV 210 nm Method F: column: Chiralpak AS-H (20 mm×250 mm, 5 μm), flow 50 mL/min, isocratic elution $MeOH:CO_2$. 25:75, detection: UV 210 nm Method G: column: Chiralpak IC (20 mm×250 mm, 5 μm), flow 50 mL/min, isocratic elution $MeOH:CO_2$, 45:55, detection: UV 210 nm Method H: column: Lux Cellulose –4 (30 mm×250 mm, 5 μm), flow 50 mL/min, isocratic elution $MeOH:CO_2$, 40:60, detection: UV 210 nm Chiral Purification Conditions—NP-HPLC Method I: column: Chiralpak IC (20 mm×250 mm, 5 μm) flow 21 mL/min, isocratic elution MeOH, detection: UV 220 nm Chiral Purification Conditions—RP-HPLC Method J: column: Lux Cellulose-2 (21 mm×150 mm, 5 μm), flow: 30 ml/min, isocratic elution, $ACN:MeOH:H_2O$, 50:20:30, detection: UV 254 nm Method K: column: Lux Cellulose-2 (21 mm×150 mm, 5 μm), flow: 30 ml/min, isocratic elution, $ACN:H_2O$, 80:20, detection: UV 254 nm Method L: column: Lux Cellulose-2 (21 mm×150 mm, 5 μm), flow: 30 ml/min, isocratic elution, $ACN:H_2O$, 65:35, detection: UV 254 nm Method M: column: Lux Cellulose-2 (21 mm×150 mm, 5 μm), flow: 30 ml/min, isocratic elution, $ACN:H_2O+ HCO_2NH_4$ (mobile phase A1), 90:10, detection: UV 254 nm Method N: column: Lux Cellulose-2 (21 mm×150 mm, 5 μm), flow: 30 ml/min, isocratic elution, $ACN:H_2O$, 70:30, detection: UV 254 nm Method O: column: Lux Cellulose-2 (21 mm×150 mm, 5 μm), flow: 30 ml/min, gradient elution, A=ACN, $B=H_2O$, detection: UV 254 nm

| Time [min] | % A | % B | Gradient curve |
|---|---|---|---|
| 0.0 | 60 | 40 | — |
| 1.0 | 60 | 40 | linear (6) |
| 5.0 | 90 | 10 | linear (6) |
| 10.0 | 60 | 40 | immediate (11) |

Method P: column: LuxAmylose-2 (21 mm×150 mm, 5 μm), flow: 30 m/min, isocratic elution, ACN:$H_2O$, 50:50, detection: UV 254 nm Method R: column: Lux Amylse-2 (21 mm×250 mm, 5 μm), flow: 30 ml/min, gradient elution; A=ACN, B=$H_2O$, detection: UV 254 nm

| Time [min] | % A | % B | Gradient curve |
|---|---|---|---|
| 0.0 | 60 | 40 | — |
| 1.0 | 60 | 40 | linear (6) |
| 7.0 | 90 | 10 | linear (6) |
| 12.0 | 60 | 40 | immediate (11) |

Method S: column: Lux Amylose-2 (21 mm×250 mm, 5 μm), flow: 30 m/min, isocratic elution, ACN:$H_2O$, 60:40, detection: UV 254 nm Method T: column: Lux Cellulose-4 (21 mm×150 mm, 5 μm), flow: 30 ml/min, isocratic elution, ACN:$H_2O$, 60:40, detection: UV 254 nm Chiral Purity Analysis Conditions—SFC Method A': column: Lux Amylse-1 (4.6 mm×250 mm, 5 μm), column temperature: 40° C., flow: 4 mL/min, isocratic elution, MeOH:CO2, 25:75, detection: UV 211 nm and 254 nm Method B': column: Lux Cellulose-1 (4.6 mm×250 mm, 5 μm), column temperature: 40° C., flow: 4 mL/min, isocratic elution, MeOH:CO2, 25:75, detection: UV 211 and 254 nm Method C': column: Lux Cellulose-4 (4.6 mm×250 mm, 5 μm), column temperature: 40° C., flow: 4 mL/min, isocratic elution, MeOH:$CO_2$, 50:50, detection: UV 210-400 nm Method D': column: Chiralpak IC (4.6 mm×250 mm, 5 μm), column temperature: 40° C., flow: 4 mL/min, isocratic elution, EtOH:$CO_2$, 45:55, detection: UV 210-400 nm Method E': column: Lux Cellulose-4 (4.6 mm×250 mm, 5 μm), column temperature: 40° C., flow: 4 mL/min, isocratic elution, MeOH:$CO_2$, 40:60, detection: UV 210-400 nm Method F': column: AMS (4.6 mm×250 mm, 5 μm), column temperature: 40° C., flow: 4 mL/min, isocratic elution, MeOH:$CO_2$, 30:70, detection: UV 211 and 254 nm Method G': column: Chiralpak IC (4.6 mm×250 mm, 5 μm), column temperature: 40° C., flow: 4 mL/min, isocratic elution, MeOH:$CO_2$, 40:60, detection: UV 210-400 nm Method H': column: Lux Cellulose-4 (4.6 mm×250 mm, 5 μm), column temperature: 40° C., flow: 4 mL/min, isocratic elution, MeOH:$CO_2$, 40:60, detection: UV 211 and 254 nm Chiral Purity Analysis—NP-HPLC Method I': column: Lux Cellulose-5 (4.6 mm×150 mm, 5 μm), column temperature: ambient, flow: 1 mL/min, isocratic elution, EtOH, detection: UV 254 nm Chiral Purity Analysis Conditions—RP-HPLC Method J': column: Lux Cellulose-2 (4.6 mm×150 mm, 5 μm), column temperature: ambient, flow: 1.23 m/min, isocratic elution, ACN:MeOH:$H_2O$, 50:20:30, detection: UV 254 nm Method K': column: Lux Cellulose-2 (4.6 mm×150 mm, 5 μm), column temperature: ambient, flow: 1.23 ml/min. isocratic elution. ACN:$H_2O$, 80:20, detection: UV 254 nm Method L': column: Lux Cellulose-2 (4.6 mm×150 mm, 5 μm), column temperature: ambient, flow: 1.23 ml/min, isocratic elution, ACN:$H_2O$, 65:35, detection: UV 254 nm Method M': column: Lux Cellulose-2 (4.6 mm×150 mm, 5 μm), column temperature: ambient, flow: 1.23 ml/min, isocratic elution, ACN:$H_2O$+$HCO_2NH_4$ (mobile phase A1), 90:10, detection: UV 254 nm Method N': column: Lux Cellulose-2 (4.6 mm×150 mm, 5 μm), column temperature: ambient, flow: 1.23 ml/min, isocratic elution, ACN:$H_2O$, 70:30, detection: UV 254 nm Method O': column: Lux Cellulose-2 (4.6 mm×150 mm, 5 μm), column temperature: ambient, flow: 1.23 ml/min, gradient elution, A=ACN, B=$H_2O$, detection: UV 254 nm

| Time [min] | % A | % B | Gradient curve |
|---|---|---|---|
| 0.0 | 60 | 40 | — |
| 1.0 | 60 | 40 | linear (6) |
| 5.0 | 90 | 10 | linear (6) |
| 10.0 | 60 | 40 | immediate (11) |

Method P': column: Lux Amylose-2 (4.6 mm×150 mm, 5 μm), column temperature: ambient, flow: 1.23 ml/min, isocratic elution, ACN:$H_2O$, 50:50, detection: UV 254 nm Method R': column: Lux Amylose-2 (4.6 mm×250 mm, 5 μm), column temperature: ambient, flow: 1.23 ml/min, gradient elution; A=ACN, B=$H_2O$, detection: UV 254 nm

| Time [min] | % A | % B | Gradient curve |
|---|---|---|---|
| 0.0 | 60 | 40 | — |
| 1.0 | 60 | 40 | linear (6) |
| 7.0 | 90 | 10 | linear (6) |
| 12.0 | 60 | 40 | immediate (11) |

Method S': column: Lux Amylose-2 (4.6 mm×250 mm, 5 μm), column temperature: ambient, flow: 1.23 ml/min, isocratic elution, ACN:$H_2O$, 60:40, detection: UV 254 nm Method T': column: Lux Cellulose-4 (4.6 mm×150 mm, 5 μm), column temperature: ambient, flow: 1.23 ml/min. isocratic elution, ACN:$H_2O$, 60:40, detection: UV 254 nm The following examples have been synthesized according to described procedures herein or known literature methods using the appropriate starting materials and methods known to the skilled person in the art

TABLE 1

| Cpd No | Structure | chiral purity analysis method | Name | Analytical Data |
|---|---|---|---|---|
| 1 | 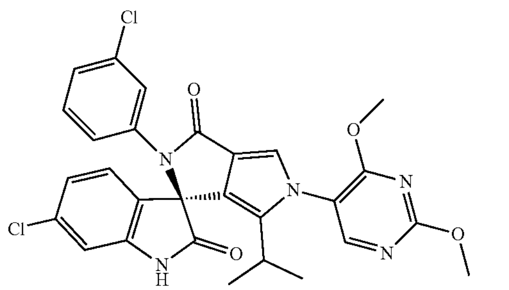 [SMILES: COc1ncc(-n2cc3c(c2C(C)C)[C@@]2(C(=O)Nc4cc(Cl)ccc42)N(c2cccc(Cl)c2)C3=O)c(OC)n1] | R' | (3S)-6-chloro-2'-(3-chlorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione | analysis in acidic gradient: 98.08%, 564 [M + H]$^+$, retention time: 3.52 min.; analysis in basic gradient: 98.13%, 564 [M + H]$^+$, retention time: 3.52 min.; chiral analysis: 99.71%, retention time: 7.77 min. |
| 2 | 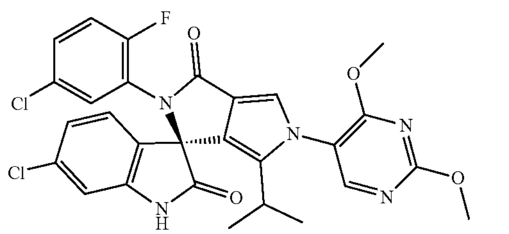 [SMILES: COc1ncc(-n2cc3c(c2C(C)C)[C@@]2(C(=O)Nc4cc(Cl)ccc42)N(c2cc(Cl)ccc2F)C3=O)c(OC)n1] | N' | (3S)-6-chloro-2'-(5-chloro-2-fluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione | analysis in acidic gradient: 99.43%, 582 [M + H]$^+$, retention time: 3.48 min.; analysis in basic gradient: 99.02%, 582 [M + H]$^+$, retention time: 3.48 min.; chiral analysis: 99.44%, retention time: 9.31 min. |
| 3 | 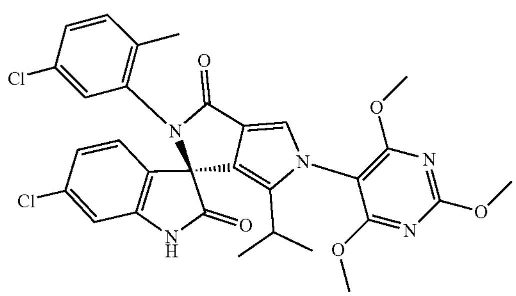 [SMILES: COc1nc(OC)c(-n2cc3c(c2C(C)C)[C@@]2(C(=O)Nc4cc(Cl)ccc42)N(c2cc(Cl)ccc2C)C3=O)c(OC)n1] | T' | (3S)-6-chloro-2'-(5-chloro-2-methylphenyl)-6'-(propan-2-yl)-5'-(2,4,6-trimethoxypyrimidin-5-yl)-1,2,3',5'-tetrahydro-2'H-spiro[indole-3,1'-pyrrolo[3,4-c]pyrrole]-2,3'-dione | analysis in acidic gradient: 97.4%, 608 [M + H]$^+$, retention time: 3.71 min.; analysis in basic gradient: 97.4%, 608 [M + H]$^+$, retention time: 3.71 min.; chiral analysis: 99.7%, retention time: 16.70 min. |
| 4 | 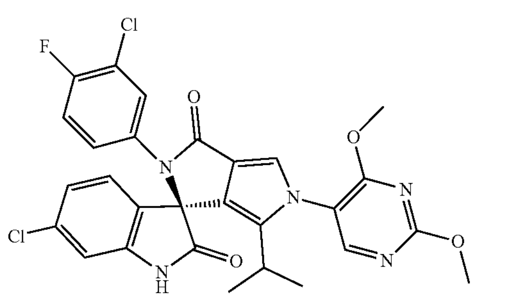 [SMILES: COc1ncc(-n2cc3c(c2C(C)C)[C@@]2(C(=O)Nc4cc(Cl)ccc42)N(c2ccc(F)c(Cl)c2)C3=O)c(OC)n1] | K' | (3S)-6-chloro-2'-(3-chloro-4-fluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione | analysis in acidic gradient: 98.96%, 582 [M + H]$^+$, retention time: 3.58 min.; analysis in acidic gradient: 99.08%, 582 [M + H]$^+$, retention time: 3.57 min.; chiral analysis: 99.97%, retention time: 3.79 min. |
| 5 | 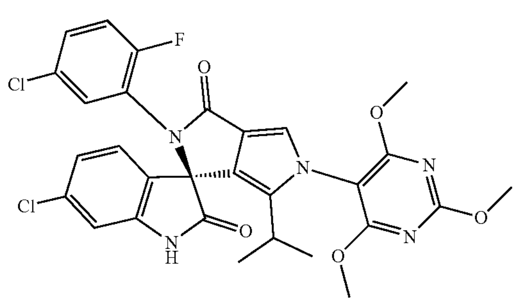 | L' | (3S)-6-chloro-2'-(5-chloro-2-fluorophenyl)-6'-(propan-2-yl)-5'-(2,4,6-trimethoxypyrimidin-5-yl)-1,2,3',5'-tetrahydro-2'H-spiro[indole-3,1'-pyrrolo[3,4-c]pyrrole]-2,3'-dione | analysis in acidic gradient: 99.89%, 612 [M + H]$^+$, retention time: 3.65 min.; analysis in basic gradient: 99.95%, 612 [M + H]$^+$, retention time: 3.65 min.; chiral analysis: 99.74%, retention time: 7.18 min. |

TABLE 1-continued

| Cpd No | Structure | chiral purity analysis method | Name | Analytical Data |
|---|---|---|---|---|
| 6 | 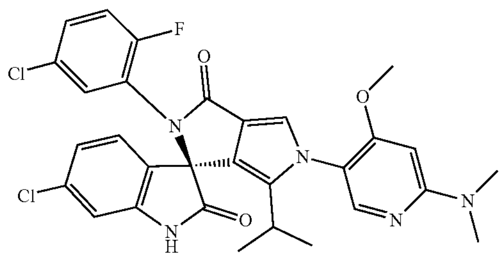 [SMILES: COc1cc(N(C)C)ncc1-n1cc2c(c1C(C)C)[C@@]1(C(=O)Nc3cc(Cl)ccc31)N(c1cc(Cl)ccc1F)C2=O] | J' | (3S)-6-chloro-2'-(5-chloro-2-fluorophenyl)-5'-[6-(dimethylamino)-4-methoxypyridin-3-yl]-6'-(propan-2-yl)-1,2,3',5'-tetrahydro-2'H-spiro[indole-3,1'-pyrrolo[3,4-c]pyrrole]-2,3'-dione | analysis in acidic gradient: 99.88%, 594 [M + H], retention time: 3.94 min.; analysis in basic gradient: 99.89%, 594 [M + H]$^+$, retention time: 3.58 min.; chiral analysis: 100%, retention time: 14.66 min. |
| 7 | 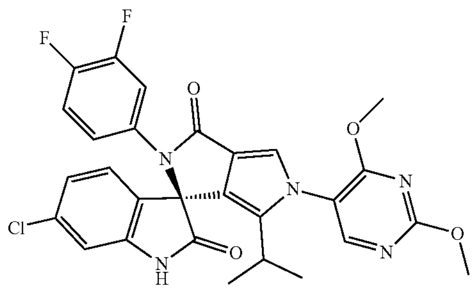 [SMILES: COc1ncc(-n2cc3c(c2C(C)C)[C@@]2(C(=O)Nc4cc(Cl)ccc42)N(c2ccc(F)c(F)c2)C3=O)c(OC)n1] | O' | (3S)-6-chloro-2'-(3,4-difluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione | analysis in acidic gradient: 98.89%, 566 [M + H]$^+$, retention time: 3.48 min.; analysis in basic gradient: 98.79%, 566 [M + H]$^+$, retention time: 3.47 min.; chiral analysis: 100%, retention time: 5.61 min. |
| 8 | 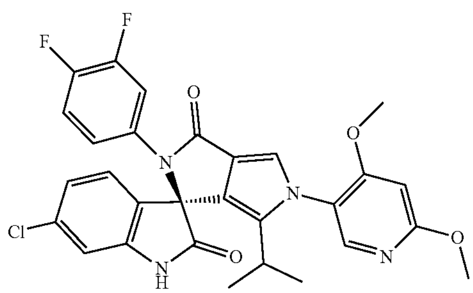 [SMILES: COc1cc(OC)c(-n2cc3c(c2C(C)C)[C@@]2(C(=O)Nc4cc(Cl)ccc42)N(c2ccc(F)c(F)c2)C3=O)cn1] | N' | (3,S)-6-chloro-2'-(3,4-difluorophenyl)-5'-(4,6-dimethoxypyridin-3-yl)-6'-(propan-2-yl)-1,2,3',5'-tetrahydro-2'H-spiro[indole-3,1'-pyrrolo[3,4-c]pyrrole]-2,3'-dione | analysis in acidic gradient: 99.75%, 565 [M + H ]$^+$, retention time: 3.57 min. analysis in basic gradient: 99.77%, 565 [M + H]$^+$, retention time: 3.57 min. chiral analysis: 100%, retention time: 6.20 min. |
| 9 | 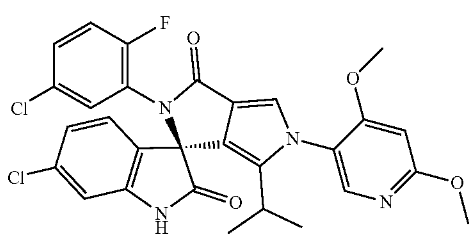 [SMILES: COc1cc(OC)c(-n2cc3c(c2C(C)C)[C@@]2(C(=O)Nc4cc(Cl)ccc42)N(c2cc(Cl)ccc2F)C3=O)cn1] | S' | (3S)-6-chloro-2'-(5-chloro-2-fluorophenyl)-5'-(4,6-dimethoxypyridin-3-yl)-6'-(propan-2-yl)-1,2,3',5'-tetrahydro-2'H-spiro[indole-3,1'-pyrrolo[3,4-c]pyrrole]-2,3'-dione | analysis in acidic gradient: 99.68%, 581 [M + H]$^+$, retention time: 3.60 min. analysis in basic gradient: 99.63%, 581 [M + H]$^+$, retention time: 3.59 min. chiral analysis: 100%, retention time: 8.85 min. |
| 10 | 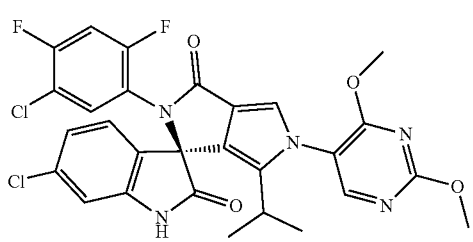 [SMILES: COc1ncc(-n2cc3c(c2C(C)C)[C@@]2(C(=O)Nc4cc(Cl)ccc42)N(c2cc(Cl)c(F)cc2F)C3=O)c(OC)n1] | P' | (3S)-6-chloro-2'-(5-chloro-2,4-difluorophenyl)-5'-(2,4-dimethoxypyrimidin-5-yl)-6'-(propan-2-yl)-1,2,3',5'-tetrahydro-2'H-spiro[indole-3,1'-pyrrolo[3,4-c]pyrrole]-2,3'-dione | analysis in acidic gradient: 97.97%, 600 [M + H]$^+$, retention time: 3.59 min. analysis in basic gradient: 97.47%, 600 [M + H]$^+$, retention time: 3.59 min. chiral analysis: 100%, retention time: 9.96 min. |

TABLE 1-continued

| Cpd No | Structure | chiral purity analysis method | Name | Analytical Data |
|---|---|---|---|---|
| 11 | 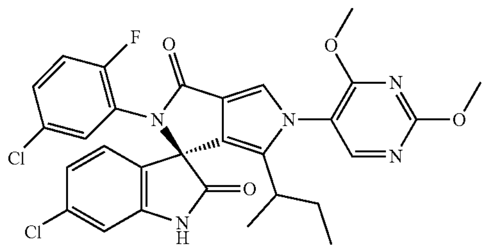 [SMILES: CCC(C)c1c2c(cn1-c1cnc(OC)nc1OC)C(=O)N(c1cc(Cl)ccc1F)[C@]21C(=O)Nc2cc(Cl)ccc21] | M' | (3S)-6-(butan-2-yl)-6-chloro-2'-(5-chloro-2-fluorophenyl)-5'-(2,4-dimethoxypyrimidin-5-yl)-1,2,3',5'-tetrahydro-2'H-spiro[indole-3,1'-pyrrolo[3,4-c]pyrrole]-2,3'-dione | analysis in acidic gradient: 97.73%, 596 [M + H]+, retention time: 3.62 min. analysis in acidic gradient: 99.54%, 596 [M + H]+, retention time: 3.62 min. chiral analysis: 100%, retention time: 9.96 min. |

Biological Examples

Biological Example 1. Fluorescent Polarization Assay

The inhibition of p53-Mdm2 interaction was measured using a fluorescence polarization (FP) binding assay. FP measures the rotational movement of molecules in a homogenous suspension. For this assay, N-terminal domain of Mdm2 protein (amino acids 1-111) is combined with a fluorescein-labeled (FAM) peptide derived from p53 transactivation domain (Sequence: 5-FAM-TSFAEYWNLLSP). Upon excitation of the fluorescent ligand with linearly polarized light the peptide emits perpendicularly polarized light. If the peptide is bound by Mdm2, rotation will slow down and the perpendicular component will proportionally decrease. In opposition disruption of the peptide-Mdm2 complex due to binding of an inhibitor to the p53 binding site of Mdm2 results in releasing of peptide and decreasing of emitted light polarization.

Fluorescence polarization experiments were read on Biotek Cytation 5 reader with the 470 nm excitation and 520 nm emission filters for fluorescein. The fluorescence polarization was measured in black 96-well plates (Corning, CLS3991) in room temperature. Purity of Mdm2 was controlled at >95%. Reaction buffer was optimized by adding 5 mM DTT and 0.1% zwitterionic detergent CHAPS to reduce effect of nonspecific interactions.

The test was performed by combining successive dilution of compounds diluted in dimethyl sulfoxide (DMSO, 5% final concentration) with 75 nM Mdm2 in reaction buffer (PBS, 0.1% CHAPS, 5 mM DTT (dithiothreitol)). After 15 minutes of incubation in room temperature 10 nM FAM-labelled peptide was added. Final reading was performed after 90 minutes of incubation. Dose-dependent binding curves and IC50 values were calculated using GraphPad Prism5 and next transformed to Ki values using Kenakin equation (Table 2).

TABLE 2

| Compound | Ki (nM) p53-Mdm2 |
|---|---|
| 1 | 1.8 |
| 2 | 1.7 |
| 3 | 2.4 |
| 4 | 1.7 |
| 5 | 2.2 |
| 6 | 1.7 |
| 7 | 1.9 |

TABLE 2-continued

| Compound | Ki (nM) p53-Mdm2 |
|---|---|
| 8 | 1.9 |
| 9 | 2.0 |
| 10 | 2.0 |
| 11 | 2.5 |

Inspection of measured Ki values shows that all the disclosed compounds are potent (Ki in range 1.7-2.5 nM) inhibitors of Mdm2-p53 interactions.

Biological Example 2. Cell Viability Assay

The effect of the invented p53-Mdm2 inhibitors on cell viability has been assessed using MTT assay. It is a colorimetric assay that measures conversion of tetrazolium ring of the soluble yellow dye (MTT) into insoluble purple formazan. This process is catalyzed solely in mitochondrial dehydrogenases of living cells. Dead cells do not cause this change. In order to measure the specific cytotoxicity of Mdm2-p53 inhibitors the MTT assay was performed with SJSA-1 osteosarcoma cell line that exhibits MDM2 gene amplification and the wild type p53.

Cells were seeded on 96-well plates and then treated with successive dilutions of tested compounds. After 72 h incubation, MTT was added to the final concentration 0.5 mg/ml. The cells were further incubated for the next 4 h. Then the solution was drained and the remaining formazan crystals were dissolved in 100 μl DMSO. The absorbance read-out was performed at 570 nm revealing the relative cell viability between cells treated with the assessed compounds and the DMSO control. All the MTT experiments were independently repeated 2-5 times. Dose-dependent binding curves and IC50 values were calculated using GraphPad Prism 5. The presented IC50 values represent the average value from all the performed experiments (Table 3).

TABLE 3

| Compound | IC50 (μM) SJSA-1 |
|---|---|
| 1 | 0.18 |
| 2 | 0.16 |
| 3 | 0.07 |
| 4 | 0.32 |
| 5 | 0.18 |
| 6 | 0.03 |
| 7 | 0.22 |
| 8 | 0.15 |
| 9 | 0.12 |

TABLE 3-continued

| Compound | IC50 (μM) SJSA-1 |
|---|---|
| 10 | 0.40 |
| 11 | 0.05 |

Biological Example 3. Measurement of In Vitro Intrinsic Clearance Using Microsomes Metabolic stability of the compounds of the invention has been assessed by measurement of the in vitro intrinsic clearance in murine and human microsomes.

10 mM stock solutions of markers and test compounds were prepared in DMSO. These were diluted 100-fold in 91:9 MeCN:DMSO to obtain a 100 μM assay stock. 10 mM NADPH was made up in 0.1M phosphate buffer (pH7.4). Microsomes were thawed in a waterbath at 37° C., and diluted to give a final assay concentration of 0.5 mg/ml.

100 μM assay stocks were added to give a final concentration of 1 μM to incubation tubes containing buffer and NADPH (final assay concentration is 1 mM). Incubation tubes and microsomes were pre-warmed at 37° C. for 3 minutes. The microsomes were then added to the incubation tubes which were kept at 37° C. and shaken using the orbital shaker for the duration of the assay. Samples were taken at 6 pre-determined time points up to 1 hour and transferred to the prepared quench tubes containing an appropriate solvent with internal standard.

Quenched samples are mixed thoroughly and protein precipitated at −20° C. for a minimum of 12 hours. Samples were then centrifuged at 4° C. Supernatants were transferred to a fresh 96 well plate, compatible with the auto-sampler. The plate was sealed with a pre-slit silicone mat and analyzed by LC-MS/MS.

| Compound | murine MS Clint [μl/min/mg] | human MS Clint [μl/min/mg] |
|---|---|---|
| WO2015/189799-107 | 9.5 | 49.7 |
| 1 | 8.8 | <3.0 |
| 2 | <4.0 | <3.0 |
| 3 | <3.0 | <3.0 |
| 4 | <3.0 | <3.0 |
| 5 | <3.0 | <3.0 |
| 6 | 33.6 | 19.8 |
| 7 | 6.6 | <3 |
| 8 | 12.8 | <3 |
| 9 | N.D. | N.D. |
| 10 | <3 | <3.2 |
| 11 | N.D. | N.D. |

In comparison to the compounds described in WO2015/189799 all the currently disclosed compounds exhibit low intrinsic clearance in both human and murine microsomes. The only exception is compound 6. However slightly less stability of this compound is compensated by outstanding in vitro efficacy (SJSA-1 IC50=0.03 μM).

Biological Example 4. In Vivo Efficacy in the SJSA-1 Xenograft Model in Mice

The experiment was conducted on female mice from the Crl:CD-1-Foxn1nu strain. Mice were inoculated subcutaneously in the right flank with cancer cell line SJSA-1 in the amount of $3 \times 10^6$ cells suspended in 100 μl HBSS: Matrigel matrix in a 3:1 ratio per mouse. On the 17th day after inoculation mice were divided into groups, so that in each group the mean tumor volume was similar and averaged around 200 mm³. Experiment groups were selected, each consisting of 8 mice: Control NaCl 0.9% and compounds. Compounds 1-11 were dissolved in 56.60% PEG 400, 9.43% Cremophor RH40, 9.43% ETOH, 18.87% Labrafil M1944CS, 5.67% DMSO. For Compound 107 from WO2015/189799, group of 7 mice was used, and it was dissolved in 15% PEG400, 10% Cremophor EL, 75% H₂O.

Mice used in the experiment were administered per os (p.o.) with compounds or NaCl 0.9% in a q1d×14 schedule (14 doses, daily). During the course of experiment mice were weighed before each administration, —twice/thrice a week. Animal welfare was monitored daily. No significant difference in body weight or welfare was observed between experiment groups during and at the end of study.

Change in tumor volume was monitored twice/thrice a week starting from the first day of administration. Tumor volume was calculated based on its length and width measured with an electronic calipers:

$V[\text{mm}^3] = d^2 \times D/2$ where d—width, D—length.

The tumor volume in the groups was measured up to 101 days after inoculation (72 days after last administration). Results of the experiment were expressed as mean values of tumor growth inhibition (TGI) ±SEM (Table 4). Tumor growth inhibition was calculated using the following formula $TGI [\%] = [100 - (T/C \times P100)]$ where C— mean tumor size in control group, T—mean tumor size in treated group. All calculations and graphs were performed using GraphPad Prism 5 software.

TABLE 4

| Compound | TGI P.O. 12.5 mg/kg (7 doses) [%] | ±SEM | TGI P.O. 12.5 mg/kg (12 doses) [%] | ±SEM |
|---|---|---|---|---|
| Reference: Compound 107 from WO2015/189799 | 49.8 | 17.3 | 60.1 | 13.4 |
| 1 | 94.97 | 1.09 | 99.53 | 0.30 |
| 2 | 94.36 | 1.23 | 98.91 | 0.44 |
| 3 | 94.22 | 1.25 | 99.57 | 0.29 |
| 4 | 94.89 | 1.57 | 99.47 | 0.34 |
| 5 | 85.78 | 5.59 | 95.99 | 2.29 |
| 6 | 92.03 | 1.88 | 99.09 | 0.46 |
| 7 | 95.00 | 1.29 | 99.97 | 0.01 |
| 8 | 96.39 | 1.57 | 99.71 | 0.27 |
| 9 | 89.46 | 2.72 | 97.73 | 0.92 |
| 10 | 93.48 | 1.44 | 98.79 | 0.50 |
| 11 | 93.74 | 1.35 | 99.69 | 0.28 |

Figure 2:
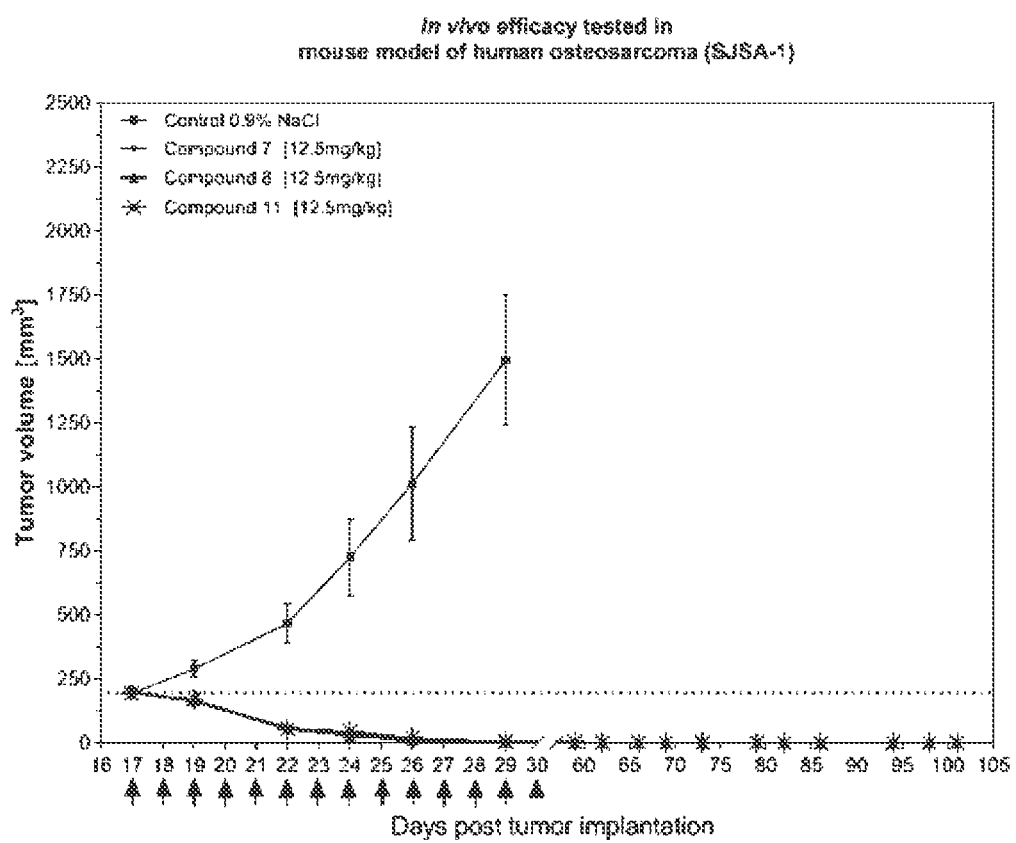
FIG. 2 shows in vivo efficacy for Compound 7, 8 and 11 of the present invention in mouse model of human osteosarcoma (SJSA-1). SJSA-1 cells were inoculated subcutaneously (s.c.) in amount of $3 \times 10^6$/mouse; the tested compounds was administered orally (p.o.) in a q1d×14 schedule; 8 mice per group.

The results of this experiment are summarized in Table 4 and FIGS. 1 and 2. As can be seen improved metabolic stability of currently disclosed compounds translates into exceptional in vivo efficacy. Tumor growth inhibition values observed for compounds 1-11 are significantly higher than for the best compound disclosed in WO2015/189799 both after 7 (difference 36.0-46.6%) and 12 (difference 35.9-39.9%) doses of a substance. Moreover as can be observed on FIG. 1 treatment of SJSA-1 xenograft with 14 doses of 12.5 mg/kg p.o. of WO2015/189799 only slows down the tumor growth. The same protocol of treatment but with compounds 7, 8 and 11 resulted in complete eradication of tumors. Moreover none of the lesions exhibited regrowth during subsequent follow-up to day 101.

The invention claimed is:

1. A compound having the following structure wherein
R¹ is meta-halo-phenyl that is unsubstituted or substituted by one to two substituents independently selected from the group consisting of halogen, —OH, —NH2, —NO$_2$, —CN, —C$_1$-C$_6$-alkyl, —O—(C$_1$-C$_6$-alkyl), —S—(C$_1$-C$_6$-alkyl), —C(O)O—(C$_1$-C$_6$-alkyl), —NH (C$_1$-C$_6$-alkyl), and —N(C$_1$-C$_6$-alkyl)$_2$,
R² and R³ are independently H or halogen;
R⁴ is —C$_1$-C$_6$-alkyl;
R⁷ is —OCH$_3$;
Z is C—R⁸ or N, Y is C—R⁹ or N, with the proviso that Z is not C—R⁸ and Y is not C—R⁹ in the same compound,
R⁵, R⁶, R⁸, R⁹ are independently H, halogen, —OCH$_3$, —NH(CH$_3$), or —N(CH$_3$)$_2$,
or a salt thereof.

2. The compound of claim 1, wherein
R¹ is meta-halo-phenyl that is unsubstituted or substituted by one to two substituents independently selected from the group consisting of halogen, C$_1$-C$_6$-alkyl, —O—(C$_1$-C$_6$-alkyl), —NH (C$_1$-C$_6$-alkyl), and N(C$_1$-C$_6$-alkyl)$_2$.

3. The compound of claim 2, wherein
R¹ is meta-halo-phenyl that is unsubstituted or substituted by one to two substituents independently selected from the group consisting of halogen, —CH$_3$, —OCH$_3$, —NH (CH$_3$), and —N(CH$_3$)$_2$.

4. The compound of claim 1, wherein
R² is H, and
R³ is Cl.

5. The compound of claim 1, wherein
R⁴ is iso-propyl or iso-butyl.

6. The compound of claim 1, wherein Z and Y are both N.

7. The compound of claim 1, wherein
Z is C—R⁸ and Y is N.

8. The compound of claim 6, wherein R⁵ and R⁶ are both OMe.

9. The compound of claim 7, wherein
R⁸ is H, and
at least one of R⁵ and R⁶ is OMe, and the second is selected from the group consisting of H, —N(Me)$_2$ and OMe.

10. The compound of claim 1, which is:

(1)
(3S)-6-chloro-2'-(3-chlorophenyl)-5'-(2,4-dimethoxypyrimidin-5-yl)-6'-(propan-2-yl)-1, 2,3', 5'-tetrahydro-2'H-spiro[indole-3,1'-pyrrolo[3,4-c]pyrrole]-2,3'-dione, (2)
(3S)-6-chloro-2'-(5-chloro-2-fluorophenyl)-5'-(2,4-dimethoxypyrimidin-5-yl)-6'-(propan-2-yl)-1, 2,3', 5'-tetrahydro-2'H-spiro[indole-3,1'-pyrrolo[3,4-c]pyrrole]-2, 3'-dione, (3)
(3S)-6-chloro-2'-(5-chloro-2-methylphenyl)-6'-(propan-2-yl)-5'-(2, 4,6-t rimethoxypyrimidin-5-yl)-1, 2,3', 5'-tetrahydro-2' H-spiro[indole-3,1'-p yrrolo[3,4-c]pyrrole]-2,3'-dione, (4)
(3S)-6-chloro-2'-(3-chloro-4-fluorophenyl)-5'-(2,4-dimethoxypyrimidin-5-yl)-6'-(propan-2-yl)-1, 2,3', 5'-tetrahydro-2'H-spiro[indole-3,1'-pyrr olo[3,4-c]pyrrole]-2, 3'-dione, (5)
(3S)-6-chloro-2'-(5-chloro-2-fluorophenyl)-6'-(propan-2-yl)-5'-(2, 4,6-t rimethoxypyrimidin-5-yl)-1, 2,3', 5'-tetrahydro-2'H-spiro[indole-3,1'-p yrrolo[3,4-c]pyrrole]-2,3'-dione, (6)
(3S)-6-chloro-2'-(5-chloro-2-fluorophenyl)-5'-[6-(dimethylamino)-4-met hoxypyridin-3-yl]-6'-(propan-2-yl)-1, 2,3', 5'-tetrahydro-2'H-spiro[indo le-3,1'-pyrrolo[3,4-c]pyrrole]-2,3'-dione, (7)
(3S)-6-chloro-2'-(3,4-difluorophenyl)-5'-(2,4-dimethoxypyrimidin-5-yl)-6'-(propan-2-yl)-1, 2,3', 5'-tetrahydro-2'H-spiro[indole-3,1'-pyrrolo[3,4-c]pyrrole]-2,3'-dione, (8)
(3S)-6-chloro-2'-(3,4-difluorophenyl)-5'-(4,6-dimethoxypyridin-3-yl)-6'-(propan-2-yl)-1, 2,3', 5'-tetrahydro-2'H-spiro[indole-3,1'-pyrrolo[3,4-c]pyrrole]-2,3'-dione, (9)
(3S)-6-chloro-2'-(5-chloro-2-fluorophenyl)-5'-(4,6-dimethoxypyridin-3-yl)-6'-(propan-2-yl)-1, 2,3', 5'-tetrahydro-2'H-spiro[indole-3,1'-pyrrol o[3,4-c]pyrrole]-2, 3'-dione,

(10)
(3S)-6-chloro-2'-(5-chloro-2,4-difluorophenyl)-5'-(2,4-dimethoxypyrimi din-5-yl)-6'-(propan-2-yl)-1, 2,3', 5'-tetrahydro-2'H-spiro[indole-3,1'-pyrrolo[3,4-c]pyrrole]-2,3'-dione, or

(11) (3S)-6'-(butan-2-yl)-6-chloro-2'-(5-chloro-2-fluorophenyl)-5'-(2,4-dimethoxypyrimidin-5-yl)-1, 2,3', 5'-tetrahydro-2'H-spiro[indole-3,1'-pyrrolo[3,4-c]pyrrole]-2,3'-dione.

11. The compound of claim 6 which is:

(1)
(3S)-6-chloro-2'-(3-chlorophenyl)-5'-(2,4-dimethoxypyrimidin-5-yl)-6'-(propan-2-yl)-1, 2,3', 5'-tetrahydro-2'H-spiro[indole-3,1'-pyrrolo[3,4-c]pyrrole]-2,3'-dione, (2)
(3S)-6-chloro-2'-(5-chloro-2-fluorophenyl)-5'-(2,4-dimethoxypyrimidin-5-yl)-6'-(propan-2-yl)-1, 2,3', 5'-tetrahydro-2'H-spiro[indole-3,1'-pyrr olo[3,4-c]pyrrole]-2, 3'-dione, (3)
(3S)-6-chloro-2'-(5-chloro-2-methylphenyl)-6'-(propan-2-yl)-5'-(2, 4,6-t rimethoxypyrimidin-5-yl)-1, 2,3', 5'-tetrahydro-2'H-spiro[indole-3,1'-p yrrolo[3,4-c]pyrrole]-2,3'-dione, (4)

(3S)-6-chloro-2'-(3-chloro-4-fluorophenyl)-5'-(2,4-dimethoxypyrimidin-5-yl)-6'-(propan-2-yl)-1, 2,3', 5'-tetrahydro-2'H-spiro[indole-3,1'-pyrrolo[3,4-c]pyrrole]-2,3'-dione, (5)

(3S)-6-chloro-2'-(5-chloro-2-fluorophenyl)-6'-(propan-2-yl)-5'-(2, 4,6-trimethoxypyrimidin-5-yl)-1, 2,3', 5'-tetrahydro-2'H-spiro[indole-3,1'-pyrrolo[3,4-c]pyrrole]-2,3'-dione, (7)

(3S)-6-chloro-2'-(3,4-difluorophenyl)-5'-(2,4-dimethoxypyrimidin-5-yl)-6'-(propan-2-yl)-1, 2,3', 5'-tetrahydro-2'H-spiro[indole-3,1'-pyrrolo[3,4-c]pyrrole]-2,3'-dione, (10)

(3S)-6-chloro-2'-(5-chloro-2,4-difluorophenyl)-5'-(2,4-dimethoxypyrimidin-5-yl)-6'-(propan-2-yl)-1, 2,3', 5'-tetrahydro-2'H-spiro[indole-3,1'-pyrrolo[3,4-c]pyrrole]-2,3'-dione, or

(11) (3S)-6'-(butan-2-yl)-6-chloro-2'-(5-chloro-2-fluorophenyl)-5'-(2,4-dimethoxypyrimidin-5-yl)-1, 2,3', 5'-tetrahydro-2'H-spiro[indole-3,1'-pyrrolo[3,4-c]pyrrole]-2,3'-dione.

12. The compound of claim 7 which is:

(6)

(3S)-6-chloro-2'-(5-chloro-2-fluorophenyl)-5'-[6-(dimethylamino)-4-methoxypyridin-3-yl]-6'-(propan-2-yl)-1, 2,3', 5'-tetrahydro-2'H-spiro[indole-3,1'-pyrrolo[3,4-c]pyrrole]-2,3'-dione, (8)

(3S)-6-chloro-2'-(3,4-difluorophenyl)-5'-(4,6-dimethoxypyridin-3-yl)-6'-(propan-2-yl)-1, 2,3', 5'-tetrahydro-2'H-spiro[indole-3,1'-pyrrolo[3,4-c]pyrrole]-2,3'-dione, or (9)

(3S)-6-chloro-2'-(5-chloro-2-fluorophenyl)-5'-(4,6-dimethoxypyridin-3-yl)-6'-(propan-2-yl)-1, 2,3', 5'-tetrahydro-2'H-spiro[indole-3,1'-pyrrolo[3,4-c]pyrrole]-2,3'-dione.

13. The compound of claim 3, wherein $R^1$ is meta-halophenyl that is substituted by one to two halogen.

14. A compound having the following structure

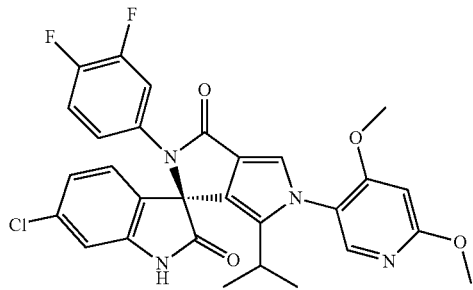 [SMILES: COc1cc(OC)c(-n2cc3c(c2C(C)C)[C@@]2(C(=O)Nc4cc(Cl)ccc42)N(c2ccc(F)c(F)c2)C3=O)cn1]

or a salt thereof.

15. A compound having the following structure

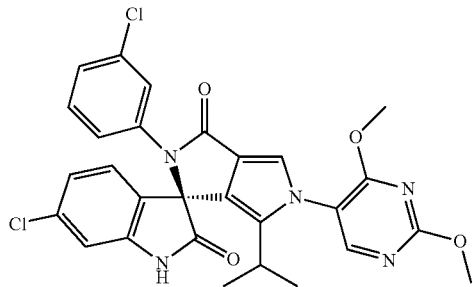 [SMILES: COc1ncc(-n2cc3c(c2C(C)C)[C@@]2(C(=O)Nc4cc(Cl)ccc42)N(c2cccc(Cl)c2)C3=O)c(OC)n1]

or a salt thereof.

16. A pharmaceutical composition comprising as an active ingredient a compound as defined in claim 1, in combination with at least one pharmaceutically acceptable excipient.

17. A pharmaceutical composition comprising as an active ingredient a compound as defined in claim 14, in combination with at least one pharmaceutically acceptable excipient.

18. A method of treating osteosarcoma comprising administering a therapeutically effective amount of the compound of claim 1 to a subject in need thereof.

19. A method of treating osteosarcoma comprising administering a therapeutically effective amount of the compound of claim 14 to a subject in need thereof.

20. A method of treating osteosarcoma comprising administering a therapeutically effective amount of the compound of claim 15 to a subject in need thereof.

* * * * *